(12) United States Patent
Gabriel

(10) Patent No.: US 8,163,151 B2
(45) Date of Patent: Apr. 24, 2012

(54) ASSAYS FOR DETECTION OF VON WILLEBRAND FACTOR (VWF) MULTIMERS AND FOR DEGRADATION OF VWF BY AGENTS SUCH AS ADAMTS13 AND RELATED METHODS

(75) Inventor: Don A. Gabriel, Carborro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 12/840,445

(22) Filed: Jul. 21, 2010

(65) Prior Publication Data

US 2010/0284996 A1 Nov. 11, 2010

Related U.S. Application Data

(63) Continuation of application No. 10/887,254, filed on Jul. 7, 2004, now Pat. No. 7,780,831.

(60) Provisional application No. 60/485,526, filed on Jul. 7, 2003.

(51) Int. Cl.
*B01D 57/02* (2006.01)
*G01N 27/00* (2006.01)
*G01N 21/00* (2006.01)

(52) U.S. Cl. ........ 204/452; 204/603; 436/164; 436/811; 356/344

(58) Field of Classification Search ............... 204/451, 204/452, 603; 436/164, 171, 811; 356/344, 356/300
See application file for complete search history.

(56) References Cited

U.S. PATENT DOCUMENTS

| 4,097,153 A | 6/1978 | DeRemigis |
| 4,648,715 A | 3/1987 | Ford et al. |
| 5,202,264 A | 4/1993 | Benson et al. |
| 5,585,278 A | 12/1996 | Vunnam et al. |
| 6,103,693 A | 8/2000 | Fischer et al. |
| 2004/0126896 A1 | 7/2004 | Hermentin et al. |

FOREIGN PATENT DOCUMENTS

| EP | 1 411 358 A1 | 4/2004 |
| JP | H8-189 | 2/1996 |
| JP | H8-211051 A | 8/1996 |

(Continued)

OTHER PUBLICATIONS

Krizek, D. R., et al., "A Rapid Method to Visualize von Willebrand Factor Multimers by Using Agarose Gel Electrophoresis, Immunolocalization, and Luminographic Detection", Thrombosis Research, vol. 97, 2000, p. 457-462.*

(Continued)

*Primary Examiner* — J. Christopher Ball
(74) *Attorney, Agent, or Firm* — Myers Bigel Sibley & Sajovec

(57) ABSTRACT

Methods of analyzing the electrophoretic mobility distribution of von Willebrand factor (vWF) multimers include providing a sample medium comprising a plurality vWF multimers. The vWF multimers are electrophoretically separated by electrohoretic mobility in the sample medium by subjecting said sample medium to an electric field to provide separated vWF multimers. The separated vWF multimers in the sample medium are exposed to a light source to produce scattered light. The scattered light is detected, and the electrophoretic mobility distribution of the separated vWF multimers is determined from the detected scattered light.

10 Claims, 5 Drawing Sheets

FOREIGN PATENT DOCUMENTS

| | | |
|---|---|---|
| JP | H10-185780 A | 7/1998 |
| WO | WO 85/04486 | 10/1985 |
| WO | WO 94/15586 | 7/1994 |
| WO | WO 95/24631 | 9/1995 |
| WO | WO 99/54360 A | 10/1999 |
| WO | WO 2000/50904 | 8/2000 |

OTHER PUBLICATIONS

Ashida et al., "Successful Treatment of a Young Infant Who Developed High-Titer Inhibitors Against VWF-Cleaving Protease (ADAMTS-13): Important Discrimination from Upshaw-Schulman Syndrome," *American Journal of Hematology*, 71:318-322 (2002).

Antoine et al., "ADAMTS13 Gene Defects in Two Brothers with Constitutional Thrombatic Thrombocytopenic Purpura and Normalization of von Willebrand Factor-Cleaving Protease Activity by Recombinant Human ADAMTS13," *British Journal of Haematology*, 120:821-854 (2003).

Binnie et al., "Parallel Characterization of Bovine von Willebrand Protein (Factor VIII-Associate Protein) by LightScattering and SDS Gel Electrophoresis," *Thrombosis Research*, 40:523-532 (1985).

Binnie, Cameron Gibson, "von Willebrand Factor and Hirudin: A Study of Two Proteins with an Effect on Coagulation," Dissertation submitted to the University of North Carolina at Chapel Hill (1989). Abstract.

Cal et al., "Cloning, Expression Analysis, and Structural Characterization of Seven Novel Human ADAMTSs, a Family of Metalloproteinases with Disintegrin and Thrombospondin-1 Domains," *Gene*, 283:49-62 (2002).

Harlow, E., *Antibodies: A Laboratory Manual*, Cold Springs Harbor Laboratory (1988).

Johnson, Jr. et al., *Laser Light Scattering*, Dover Press, NY (1994).

Kempfer et al., "Requirement of a Plasma Fraction for the Loss of Large von Willebrand Factor Multimers Induced by High Wall Shear Rate," *Medicina*, (Buenos Aires), 57(4):409-416 (1997).

Levy et al., "Mutations in a Member of the Adamts Gene Family Cause Thrombotic Thrombocytopenic Purpura," *Nature*, 413:488-494 (2001).

Li et al., "The Physical Exchange of Factor VIII (FVIII) between von Willebrand Factor and Activated Platelets and the Effect of the FVIII B-Domain on Platelet Binding," *Biochemistry*, 36:10760-10767 (1997).

Loscalzo et al., "Subunit Structure and Assembly of von Willebrand Facotr Polymer. Complementary Analysis by Electron Microscopy and Quasielastic Light Scattering," *Biophys. J.*, 49:49-50 (1986).

Loscalzo et al., "Solution Studies of the Quaternary Structure and Assembly of Human von Willebrand Factor," *Biochemistry*, 24:4468-4475 (1985).

Mannucci et al., "Changes in Health and Disease of the Metalloprotease that Cleaves von Willebrand Factor," *Blood*, 98(9):2730-2735 (2001).

Mauz-Körholz et al., "DDAVP Treatment in a Child with von Willebrand Disease Type 2M," *Eur. J. Pediatr.*, 3:S174-S176 (1999).

Perutelli, Paolo, "Proteolysis of von Willebrand Factor is Increased During Cardiopulmonary Bypass," *Thrombosis Research*, 102:467-473 (2001).

Pethica, B.A., "The Physical Chemistry of Cell Adhesion," *Experimental Cell Research*, 8:123-140 (1961).

Sadler et al., "von Willebrand Disease: Diagnosis, Classification, and Treatment," Chapter 51, 825-837 *Colman, RW. Hemostatics and Thrombosis,Basic Principles and Clinical Practice*, 4th ed. (2000).

Schneppenheim et al., "von Willebrand Factor Cleaving Protease and ADAMTSI3 Mutations in Childhood TTP," *Blood*, 101(5):1845-1850 (2003).

Slayter et al., "Native Conformation of Human von Willebrand Protein. Analysis by Electron Microscopy and Quasi-Elastic Light Scattering," *The Journal of Biological Chemistry*, 260(14):8559-8563 (1985).

Ware, B.R., "Electrophoretic Light Scattering", *Advance in Colloid and Interface Science*, 4:1-44 (1974).

Zheng et al., "Structures of von Willebrand Factor-Cleaving Protease (ADAMTSI3), a Metalloprotease Involved in Thrombotic Thrombocytopenic Purpura," *The Journal of Biological Chemistry*, 276(44):41059-41063 (2001).

Barington et al., "A Very-High-Purity von Willebrand Factor Preparation Containing High-Molecular-Weight Multimers," http://BioMedNet.com/karger pp. 85-89 (1999).

Budde et al., "von Willebrand Factor and von Willebrand Disease," *Rev Clin Exp Hematol*, 54:335-368 (Dec. 2001).

Budde et al., "Luminographic Detection of von Willebrand Factor Multimers in Agarose Gels and on Nitrocellulose Membranes," *Thrombosis and Haemostasis*, Stuttgart, DE, 63(2):312-315 (1990).

Chung et al., "Processing of von Willebrand Factor by ADAMTS-13," *Biochemistry, American Chemical Society*, 41(37): 11065-11070 (Sep. 17. 2002).

Dash et al., "Synthetic Polymers for Vectorial Delivery of DNA: Characterization of Polymer-DNA Complexes by Photon Correlation Spectroscopy and Stability to Nuclease Degradation and Disruption by Polyanions in Vitro," *Journal of Controlled Release*, 48(2,3): 269-276 (Oct. 13, 1997).

Furlan et al., "Assays of VonWillebrand Factor-Cleaving Protease: A Test for Diagnosis of Familial and Acquires Thrombotic Thrombocytopenic Purpura," *Seminars in Thrombosis and Hemostasis*, Stuttgartm DE, 28(2): 167-172 (Apr. 2002).

Gao et al., "Capillary Electrophoresis and Synamic Light Scattering Studies of Structure and Binding Characteristics of Protein-Polyelectrolyte complexes," *J. Phys. Chem.* 102:5529-5535 (1998).

Smejkal et al., "Rapid High-Resolution Electrophoresis of Multimeric von Willebrand Factor Using a Thermopiloted Gel Apparatus," *Electrophoresis*, 24(4): 582-587 (Feb. 2003).

Tsai, Km., "Von Willebrand Factor, ADAMTSI3 and Thrombotic Thrombocytopenic Purpura." *Journal of Molecular Medicine*, 80(10): 639-647 (Oct. 2002).

Webb, C.E., "Analysis of VonWillebrand Factor (VWF) Multimers in Acquired Haemostatic Disorders," *Ph.D. Council for National Academic Awards* (UK), 239 pages (1989).

Xia et al., "Electrophoretic and Quasi-Elastic Light Scattering of Soluble Protein-Polyelectrolyte Complexes," *Journal of Physical Chemistry*, 97:4528-4534, 1993.

Xiao et al., "Solution Stability of Von Willebrand Factor (vWF) as Observed by Photon Correlation Sprectroscopy (PCS)," *37th Annual Meeting of the American Society of Hematology*, Seattle, Washington, 86(10) suppl. 1: 879A (Dec. 1-5, 1995). Meeting Abstract. Database Biosis, '*Online Biosciences Information Service*,' Abstract No. PREV19969862332.

International Search Report for PCT/US04/021715; Date of mailing Dec. 16, 2004.

Robert K. Andrews; Purification of Botrocetin from *Bothrops jararaca* Venom. Analysis of the Botrocetin-Mediated Interaction between von Willebrand Factor and the Human Platelet Membrane Glycoprotein Ib-IX Complex; Biochemistry 1989, 28, pp. 8317-8326.

Japanese Office Action dated May 14, 2010, Dispatch No. 329767 for Japanese Patent Application No. 2006-518867 with English Translation.

EPO Examination Report for Application No. 04 777 665.3—2404 dated Aug. 24, 2010.

Office Action dated Jan. 18, 2010 corresponding to Japanese Patent Application No. 2006-518867; 5 pages.

Perutelli; Haematologica 2002; 87:223-224; vol. 87(2) Feb.

Communication pursuant to Article 94(3) EPC; for Application No: 04 777 665.3 -2404 mailed Dec. 21, 2011.

Matsui et al., "3-D Structure and Function of Botrocetin", a von Willebrand Factor Modulator Protein, Journal of Thrombosis and Hemostasis, 2001, vol. 12(6), p. 240-245. (Concise explanation of relevance provided in Translation of Office Action for Japanese Application No. 2006-51887).

Translation of Office Action for Patent Application No. JP 2006-518867; mailed on Dec. 16, 2011.

\* cited by examiner

ASSAYS FOR DETECTION OF VON WILLEBRAND FACTOR (VWF) MULTIMERS AND FOR DEGRADATION OF VWF BY AGENTS SUCH AS ADAMTS13 AND RELATED METHODS

RELATED APPLICATIONS

This application is a continuation of and claims priority to U.S. patent application Ser. No. 10/887,254, filed Jul. 7, 2004 now U.S. Pat. No. 7,780,831, which claims priority from U.S. Provisional Application Ser. No. 60/485,526 filed Jul. 7, 2003, the disclosures of which are hereby incorporated by reference in their entirety.

FIELD OF THE INVENTION

The present invention generally relates to methods and systems for spectroscopy, and more specifically, to electrophoretic spectral techniques.

BACKGROUND OF THE INVENTION

Von Willebrand factor (vWF) is a polydispersed multimeric plasma glycoprotein, which participates in the initial platelet adhesion and transport of coagulation FVIII. The size distribution of vFW multimers has a critical effect on its function, since the larger the vWF multimer, the more effective it is in promoting platelet adhesion. However, if ultra large multimers are present, spontaneous platelet aggregation and adhesion can occur and produce a thrombophilic state.

Recent studies have shown that ADAMTS13 (A Disintegrin-like And Metalloprotease with ThromboSpondin type 1 motif), a proteolytic enzyme synthesized primarily in the liver, is responsible for proteolysis of vWF within its A2 domain. A deficiency of ADAMTS13 will result in the presence of uncleaved ultra large vWF multimers, a circumstance not commonly observed in normal plasma [Levy, G. G. et al. *Nature* 413:488-494 (2001)]. In addition, these studies suggest that levels of activity and inhibition of this metalloprotease may be useful in the diagnosis and treatment of patients with thrombotic thrombocytopenia purpura (TTP) [Mannucci P. et al. 98:2730-35 (2001)]. There are several different manifestations of ADAMTS13 abnormalities. In congenital TTP, ADAMTS13 is found to be quantitatively deficient. With acquired TTP, an IgG autoantibody is formed that inhibits ADAMTS13. In other forms of acquired TTP/HUS (hemolytic uremic syndrome), ADAMTS13 may be present in variable concentrations. For example, deficiencies of ADAMTS 13 can result from *E. Coli* infections in children, veno-occlusive disease in bone marrow transplant, and a wide variety of drug toxicities.

The laboratory diagnosis and subtyping of vWF has been challenging since vWF does not appear on routine diagnostic blood tests. Physicians therefore must order specialized diagnostic blood tests to determine the specific vWF variant in order to establish the best and safest treatment for each patient.

Several types of assays currently exist for diagnosing vWF abnormalities. In the use of such assays, the vWF antigen must be determined for proper diagnosis. These assays variously include: radioimmunoassay (RIA) involving competitive binding of radiolabeled antigen and unlabeled antigen to a high-affinity antibody; enzyme immunoassay (EIA) and enzyme-linked immunosorbent assay (ELISA) [see U.S. Pat. No. 5,202,264] employing color reaction products of enzyme substrate interaction to measure antigen-antibody reaction; and latex immunoassay (LIA) utilizing antibodies bound at their Fv region to latex particles and presenting a Fab region for interaction with antigens present in blood samples [see U.S. Pat. No. 5,585,278].

The foregoing immunoassays are simple and widely used, but suffer several disadvantages. The immunoassays require labeled antibodies, which can be quite expensive and entail intrinsic hazards when radioactive labels are used. In addition, the occurrence of non-specific binding of proteins to antigens, the formation of antibody complexes, and the presence of various types of commonly used solid supports, can each increase background noise and reduce sensitivity, with the result that false-positive determinations are made [Harlow, E. *Antibodies: A Laboratory Manual*, Cold Springs Harbor Laboratory 1988].

Traditionally, abnormalities in vWF associated with disease states are further confirmed and classified into subtypes by multimeric structure and size distribution analysis of vWF using Western Blot electrophoresis. In principle, as many as 40 different molecular weight polymers are possible based on a dimer Mr of 500,000 and an upper limit molecular weight of 20 million. Current assessment of vWF multimer size distribution using Western Blot electrophoresis shows 10 to 15 distinct major electrophoretic mobilities. This classical and current method is used to detect epitopes of electrophoretically separated subspecies of antigens resulting in a spectral distribution of multimers by electrophoretic mobility. Electrophoresis of known molecular weight standards allows for the determination of the molecular weight of each antigenic band to which antibodies may be produced [Colman R W. Hemostasis and Thrombosis, Basic Principles and Clinical Practice, $4^{th}$ edition; pp 825-837]. The disadvantages of this method can include: its substantial cost; its typical requirement of 3-5 days for completion of analysis, the need for a reporter group to label anti-vWF antibodies with radioactivity, fluorescence, or chemiluminescence for identification of multimers; and its reduced resolution of high and ultra-large molecular weight multimers.

Further, vWF related diseases involve the persistent diagnostic problem of non-specific bleeding symptoms. Current diagnostic testing for vWF is of limited value when low values for vWF:RCO (ristocetin co-factor) and vWF:Ag are present, due to the broad range of normal values of plasma vWF concentration. Compounding the difficulty is the fact that bleed times have an even wider normal variation than vWF levels. Therefore, the previously known tests do not provide the high level of precision that is essential to the accurate and reliable diagnosis of vWF related diseases.

Currently, there is a strong need for diagnostic tests that would be cost-effective, efficient, and provide additional molecular information benefiting the physician, laboratory and patient.

SUMMARY OF THE INVENTION

According to embodiments of the present invention, methods and systems for physically characterizing vWF multimers are provided. vWF multimer distribution, concentration, diffusion coefficient, and size may be determined. For example, the electrophoretic mobility distribution of vWF multimers in a sample medium can be determined. The electrophoretic mobility distribution can be used to calculate, for example, the size, concentration, diffusion coefficient, weight and distributions thereof for vWF multimers in the sample medium.

In some embodiments of the present invention, methods of analyzing the electrophoretic mobility distribution of von Willebrand factor (vWF) multimers include providing a sample medium comprising a plurality vWF multimers. The vWF multimers are electrophoretically separated by electrophoretic mobility in the sample medium by subjecting the sample medium to an electric field to provide separated vWF multimers. The separated vWF multimers in the sample medium are exposed to a light source to produce scattered light. The scattered light is detected, and the electrophoretic mobility distribution of the separated vWF multimers is determined from the detected scattered light.

In some embodiments, a vWF abnormality and/or disease is identified based on the electrophoretic mobility distribution. The vWF abnormality and/or disease may be selected from the group consisting of Type I vWF disease, Type II vWF disease, Type III vWF disease, subtype IIA vWF disease, subtype IIB vWF disease, subtype IIM vWF disease, thrombotic thrombocytopenic purpura (TTP), and hemolytic uremic syndrome (HUS). For example, the electrophoretic mobility distribution can be compared to parameters corresponding to a set of vWF abnormalities and/or diseases. The parameters can be based on a plurality of spectra corresponding to the set of vWF abnormalities and/or diseases. In some embodiments, an ADAMTS abnormality and/or disease can be identified based on the electrophoretic mobility distribution.

In some embodiments, a photon correlation spectroscopy (PCS) spectrum of the sample medium can be generated and a molecular size distribution can be determined based on the PCS spectrum of the sample. A vWF abnormality and/or disease can be identified based on the molecular size distribution and the electrophoretic mobility distribution. Thus, electrophoretic and non-electrophoretic spectroscopy techniques may be combined to determine whether a vWF abnormality exists in the sample medium.

Determining the electrophoretic mobility distribution may be carried out by electrophoretic quasi elastic light scattering analysis. For example, a phase shift can be detected in the scattered light from a measured autocorrelation function. A Doppler shift can be detected in the scattered light compared to the incident light. Then the electrophoretic mobility of the scattering particle can be calculated.

The light source can be a coherent light source. The sample medium can be provided in a container; and the electrophoretically separating step can be carried out with the sample medium in the container. The exposing step and he detecting step may both be carried out with the solution in the container. In some embodiments, the container can define or include a capillary zone to facilitate capillary spectroscopic determinations of vWF abnormality and/or disease in the sample medium, such as by capillary zone electrophoresis techniques.

In some embodiments, the electrophoretically separating step, the exposing step, and the detecting step are carried out in a total time of less than 5 minutes, e.g., less than 1 minute.

The determined electrophoretic mobility distribution can include vWF multimers having a molecular weight of up to 10 million, 20 million or more.

In some embodiments, the step of providing a sample medium is carried out by providing a plasma sample, and purifying vWF from the plasma sample to provide the sample medium. The von Willebrand factor (vWF) multimers can be human von Willebrand factor multimers.

According to further embodiments of the present invention, methods of determining the presence of a von Willebrand factor (vWF) degrading enzyme in a sample medium include providing a sample medium comprising an amount of vWF multimers. A specimen suspected of containing a vWF degrading enzyme is added to the sample medium so that high molecular weight vWF multimers in the sample medium are degraded when an enzyme is present in the sample. The vWF multimers are electrophoretically separated by electrophoretic mobility in the sample medium by subjecting the sample medium to an electric field to provide separated vWF multimers. The separated vWF multimers in the sample medium are exposed to a light source to produce scattered light. The scattered light is detected and the electrophoretic mobility distribution of the separated vWF multimers is determined from the detected scattered light. The presence or absence of the vWF degrading enzyme is determined from the electrophoretic mobility distribution.

In some embodiments, a photon correlation spectroscopy (PCS) spectrum of the sample medium is generated. A molecular size distribution is determined based on the PCS spectrum of the sample medium. The presence or absence of the vWF degrading enzyme can be determined based on the molecular size distribution and the electrophoretic mobility distribution. The vWF degrading enzyme can be ADAMTS13.

According to further embodiments of the present invention, systems for analyzing the electrophoretic mobility distribution of von Willebrand factor (vWF) multimers in a sample medium include an Electrophoretic Quasi-elastic Light Scattering (EQELS) spectrometer comprising an EQELS controller configured to electrophoretically separate the vWF multimers and to generate a EQELS spectrum for the vWF multimers in the sample medium. An EQELS analyzer is in communication with the EQELS spectrometer. The EQELS analyzer is configured to determine the electrophoretic mobility distribution of the separated vWF multimers from the EQELS spectrum. The system can be used to carry out various steps described herein. In some embodiments, the EQELS spectrometer is further configured to generate a photon correlation spectroscopy (PCS) spectrum of the sample medium. For example, the electric field in the EQELS spectrometer may be deactivated for PCS spectroscopy. The EQELS analyzer is further configured to determine a molecular size distribution based on the PCS spectrum of the sample medium.

According to further embodiments of the present invention, methods of detecting electrophoretic mobility and/or size distribution characterization of vWF multimers in a sample medium include impinging energy on the sample medium to generate an energy interaction output. An electrophoretic mobility distribution and/or size distribution of vWF multimers in the sample medium is determined based on the energy interaction output.

For example a presence, absence, and/or relative amount of ones of the vWF multimers in the sample medium can be determined based on the electrophoretic mobility distribution and/or size distribution of the vWF multimers. Impinging energy can include impinging light energy on the sample medium. A size distribution of vWF multimers can be determined using photon correlation spectroscopy (PCS) static light scattering, electrophoretic quasi-elastic light scattering (EQELS) and/or capillary zone electrophoresis (CZE) dynamic light scattering.

The sample medium can include plasma or components thereof and/or a dilute buffer salt solution. The energy interaction output can be produced under electrophoretic or non electrophoretic (PCS) conditions.

The sample medium can be provided by adding an amount of high molecular weight vWF to a plasma sample derived from a subject. A presence or absence of a vWF-metabolic enzyme in the plasma sample can be determined based on the electrophoretic mobility and/or size distribution of vWF multimers in the sample medium. The vWF-metabolic enzyme can include ADAMTS13 and/or enzymes that metabolize vWF in the release of vWf from an endothelium. A presence or absence of a vWF metabolic product fragment having a molecular weight of 176,000 Mr. can be determined to determine the presence or absence of the vWF-metabolic enzyme. A diagnosis for the subject can be generated based on the presence or absence of the vWF-metabolic enzyme in the plasma sample derived from the subject. A diagnosis for the subject can be generated based on the presence or absence of a vWF metabolic product fragment having a molecular weight of 176,000 Mr. For example a presence of or absence of, or susceptibility to, a physiological condition associated with a deficiency of the vWF-metabolic enzyme in the plasma sample can be determined based on the electrophoretic mobility and/or size distribution of the vWF multimers in the sample medium. A presence of or absence of, or susceptibility to, a physiological condition associated with a deficiency of ADAMTS13 in the plasma sample can be determined based on the electrophoretic mobility and/or size distribution of the vWF multimers in the sample medium. The physiological condition can include a disease state selected from the group consisting of TTP, HUS, TTP/HUS, diseased states that causes abnormal function of endothelium to release vWF, Acute Coronary Syndrome, Diabetes, Hypertension, Menorraghia, and/or Renal Failure.

In some embodiments, the subject can be administered a therapeutic agent and/or procedure that is potentially effective to increase a presence of the vWF-metabolic enzyme in the subject. An electrophoretic mobility and/or size distribution of vWF can be determined from a first sample taken from the subject before administering the therapeutic agent and/or procedure and from a second sample taken from the subject after administering the therapeutic agent. An effectiveness of the therapeutic agent and/or procedure can be assessed based on the electrophoretic mobility and/or size distributions of vWF from the first and second samples. The therapeutic agent can include a potentially therapeutically effective amount of an ADAMTS13 protease selected from the group consisting of: recombinant ADAMTS13; synthetic ADAMTS13; mutants, variants, fragments and fusions of recombinant ADAMTS13; and mutants, variants, fragments and fusions of synthetic ADAMTS13. The vWF-metabolic enzyme can include ADAMTS13.

According to further embodiments of the present invention, methods of identifying a subject as having or being at risk of developing a disease state or physiological condition associated with an absence or deficiency of ADAMTS13 includes: obtaining from the subject a physiological sample of a type in which ADAMTS13 is present in a normal subject; adding to the physiological sample an amount of high molecular weigh (HMW) vWF to provide a sample medium; performing static and/or dynamic light scattering spectroscopy on the sample medium to determine an electrophoretic mobility distribution and/or size distribution of vWF multimers attributable to degradation of the HMW vWF by ADAMTS13; and identifying the subject as having or being at risk of developing a disease state or physiological condition associated with an absence or deficiency of ADAMTS13 based on the electrophoretic mobility distribution and/or size distribution of vWF multimers.

The static and/or dynamic light scattering spectroscopy may be carried out using electrophoretic quasi elastic light scattering (EQELS), photon correlation spectroscopy (PCS), and/or capillary zone electrophoresis (CZE).

It can be determined whether the electrophoretic mobility distribution and/or size distribution of vWF multimers includes a vWF fragment having a molecular weight of 176, 000 Mr. The sample medium can be purified, for example, using chromatographic purification.

The sample medium can include a reagent that binds to the HMW vWF and/or vWF multimers attributable to the metabolism of the HMW vWF by ADAMTS13 and that alters mobility characteristics of the HMW vWF and/or vWF multimers when bound thereto for enhanced determination of the electrophoretic mobility and size distribution. The reagent can include Botricetin.

According to further embodiments of the present invention, methods of treating a subject with a disease state or physiological condition associated with an absence or deficiency of an enzyme effective to metabolize vWF include: administering to the subject a therapeutic agent for combating the absence or deficiency of the enzyme; after administering the therapeutic agent, obtaining from the subject a physiological sample of a type in which the enzyme is present in a normal subject; adding to the physiological sample an amount of HMW vWF; performing static and/or dynamic light scattering spectroscopy on the sample medium to determine an electrophoretic mobility distribution and/or size distribution of vWF multimers attributable to metabolism of the HMW vWF by the enzyme; and determining the efficacy or non-efficacy of the therapeutic agent based on the electrophoretic mobility distribution and/or size distribution of vWF multimers.

The therapeutic agent can include an agent that potentially increases the amount of the enzyme in the subject. A collagen binding assay can be used for vWF multimer characterization. vWF defectively binding coagulation FVIII can be characterized using a vWF Normandy assay. vWF for HMW vWF multimers and ultra large vWF multimers can also be characterized. A disease state or physiological condition can be diagnosed including disease states or physiological conditions selected from the group consisting of: septicemia, acute coronary artery syndrome, veno-occlusive disease, drug toxicity and acute inflammation based on the electrophoretic mobility distribution and/or size distribution of vWF multimers.

According to further embodiments of the present invention, a system for identifying a subject as having or being at risk of developing a disease state or physiological condition associated with an absence or deficiency of an enzyme mediating metabolism of vWF is provided. The system includes: a means for obtaining from the subject a physiological sample of a type in which ADAMTS13 is present in a normal subject; a means for adding to the physiological sample an amount of high molecular weigh (HMW) vWF to provide a sample medium; a means for performing static and/or dynamic light scattering spectroscopy on the sample medium to determine an electrophoretic mobility distribution and/or size distribution of vWF multimers attributable to degradation of the HMW vWF by ADAMTS13; and a means for identifying the subject as having or being at risk of developing a disease state or physiological condition associated with an absence or deficiency of ADAMTS13 based on the electrophoretic mobility distribution and/or size distribution of vWF multimers.

According to further embodiments, an assay kit for the rapid determination of an absence or deficiency of an enzyme mediating metabolism of vWF in a subject is provided. The kit includes a means for obtaining an amount of a physiological sample from a subject of a type in which the enzyme is present in a normal subject; an amount of HMW vWF for addition to the physiological sample, to provide a sample medium for static light scattering methods and/or dynamic light scattering methods including EQELS (Electophoretic Quasi Elastic Light Scattering, PCS (Photon Correlation Spectroscopy) and the like or CZE (Capillary Zone Electrophoresis) analysis of electrophoretic mobility and size distribution of vWF multimers therein attributable to metabolism of the HMW vWF by the enzyme, wherein an absence or deficiency of the enzyme in the subject is determinable.

Among other things, assays of the present invention are useful for screening subjects, particularly human subjects or other mammalian subjects for disorders related to vWF and/or ADAMTS13, including but not limited to von Willebrand disease, thrombotic thrombocytopenic purpura (TPP)/hemolytic Uremic Syndrome (HUS), etc.

DETAILED DESCRIPTION OF EMBODIMENTS OF THE INVENTION

Figure 1:
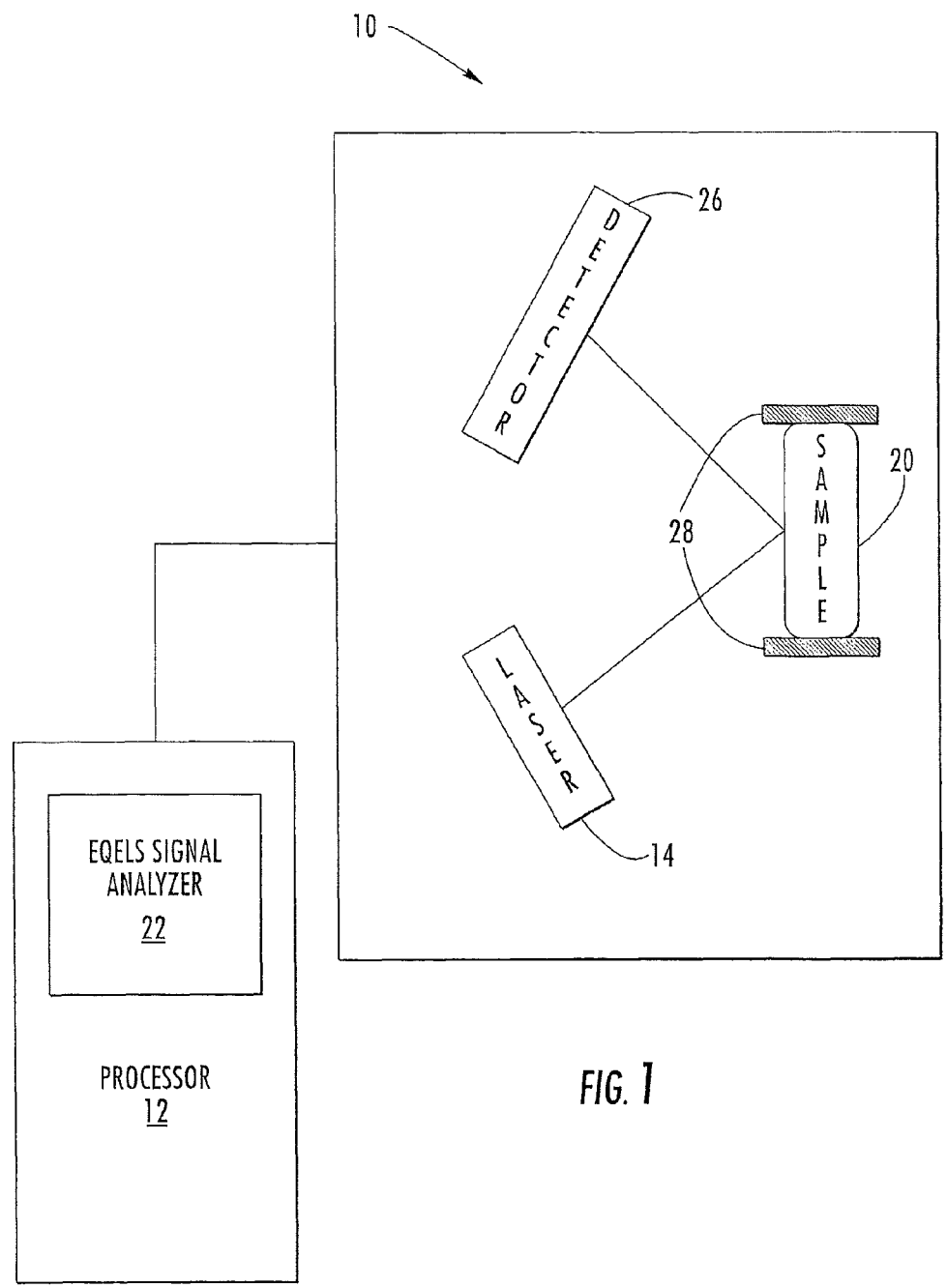
FIG. 1 is a block diagram of an Electrophoretic Quasi-elastic Light Scattering (EQELS) spectrometer according to embodiments of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. Elements in the various figures are not drawn to scale and may be enlarged to show detail.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Embodiments of the present invention provide a methodology for the rapid characterization of vWF and vWF-metabolic agents such as ADAMTS13 in media containing same, e.g., in physiological samples or solutions including physiological samples or components thereof. vWF is a polymeric plasma glycoprotein that exists in plasma as a series of multimers of varying molecular weights. Various spectroscopy techniques may be used to probe the vWF multimers in a sample to characterize the sample, for example, based on the electrophoretic mobility, molecular weight distribution, molecular size distribution, and/or the diffusion coefficients of multimers in the sample.

Although embodiments of the present invention are described with respect to Electrophoretic Quasi-elastic Light Scattering (EQELS) spectroscopy, it should be understood that other electrophoretic interaction spectral techniques (i.e., techniques in which a biological particle in an electrophoretic field interacts with an energetic medium to generate a spectrum) and/or non-electrophoretic techniques can be used. Spectroscopy techniques that do not employ an electrophoretic field include photon correlation spectroscopy (PCS).

Moreover, although embodiments of the present invention are described with respect to an excitation light beam, other energetic media can be used, including electromagnetic energy, acoustic energy, ultrasonic energy, or other suitable energy media. For example, electromagnetic energy can be employed from any suitable spectral range, such as visible light, infrared, ultraviolet, and/or x-ray ranges. For example, actinic radiation having a wavelength from about 200 nm to about 700 nm can be used as an energetic medium for interaction with vWF multimers in an electrophoretic field. Visible light radiation can be used in light-scattering techniques, including elastic light scattering and quasi-elastic light scattering. Ultraviolet radiation can be used, for example, in capillary electrophoresis systems having an ultraviolet laser as an energy source for ultraviolet radiation impinged on a biological particle in the capillary flow stream. Thus, any suitable energy source and corresponding energy medium can be used.

In some embodiments, characteristics of a spectrum from a sample are used to diagnose various conditions, such as the degradation of high molecular weight vWF, thrombotic thrombocytopenic purpura (TTP) and thrombotic thrombocytopenic purpura/hemolytic uremic syndrome (TTP/HUS). Treatments of these conditions may also be evaluated, for example, by comparing spectra obtained before and after treatment. Moreover, agents that interact with vWF multimers, such as vWF-metabolic agents including ADMTS13, may be evaluated using the spectroscopy techniques described herein. For example, spectra from a vWF sample may be taken before and after an agent is added to the sample to compare the effect of the agent on the vWF multimers.

Subjects from whom samples may be collected in carrying out the present invention include human subjects, for medical and diagnostic purposes, as well as other animal subjects, particularly mammalian subjects such as dogs, cats, rats, pigs, horses, sheep, cattle, monkeys, etc., for veterinary and drug development purposes.

Von Willebrand Factor (vWF) is known and described in, for example, U.S. Pat. Nos. 6,531,577; 6,518,482; 6,465,624; 6,410,237; 6,103,693; and 6,040,143, the contents of which are incorporated herein by reference. vWF used in the present invention may be natural or recombinant, and where natural may be collected from a subject for diagnostic purposes or harvested from a subject for the preparation of a therapeutic composition.

ADAMTS13 (A Disintegrin-like And Metalloprotease (reprolysin type), with ThromboSpondin type 1 motif) is known and described in, for example, G. Antoine et al., *Br. J. Haematol.* 70, 257-262 (2003); R. Schneppenheim et al., *Blood* 101, 1845-1850 (2003); A. Ashida et al., *Am. J. Hematol.* 71, 318-322 (2002); S. Cal et al., *Gene* 283, 49-62 (2002); X. Zheng et al., and *J. Biol. Chem.* 276, 41059-41063 (2001). ADAMTS13 or other ADAMTS enzymes used in accordance with embodiments of the present invention may be natural or recombinant, and where natural may be collected from a subject for diagnostic purposes or harvested from a subject for the preparation of a therapeutic composition.

Embodiments of the present invention can be used to detect high molecular weight vWF multimers and ultra large vWF multimers. The normal range of vWF multimer weights is from 500,000 to 20,000,000. Molecular weights from 10 to 20 million are considered "high molecular weight" (HMW) multimers. As used herein, the term "ultra large multimer" in reference to vWF, means von Willebrand Factor multimer having a molecular weight of greater than 20 million Mr. Ultra large multimers are include monomers greater than 20 million, and can be as high as 100,000,000, and are encompassed by the phrase "high molecular weight multimers" or "HMW" or the like herein.

By way of background to the ensuing discussion, set out below is a discussion of the various spectral techniques.

Dynamic light scattering (DLS) involves particle-mediated scattering of light that is impinged on an inhomogeneous (particle-containing) medium and the measurement of the temporal autocorrelation function for a scattering vector at a specific scattering angle. From a scattering intensity and the autocorrelation function, one can determine particle size (hydrodynamic radii), shape factors and/or other characteristics of the particles in the particle-containing medium. Dynamic light scattering is also referred to as photon correlation spectroscopy (PCS).

Electrophoretic quasi-elastic light scattering (EQELS) is a dynamic light scattering technique in which an electric field is imposed on the sample for characterizing particles in a medium, which utilizes electrophoresis, in which particles are characterized by their movement in an applied electric field. Capillary zone electrophoresis (CZE) uses a very high electric field to induce particle mobility through a narrow tube driven by electroosmosis. The particle can then be characterized with respect to size and particle surface charge. These techniques may be used for the characterization of vWF multimers in media containing the same and may employ a superimposed electric field to freely allow these multimers to electrophorese. The electrophoretic mobility of the multimers in the solution depends on both the size of the multimer, the total charge of the multimer, and the strength of the superimposed field.

Thus, embodiments of the present invention are carried out with Electrophoretic Quasi Elastic Light Scattering (EQELS), capillary zone electrophoresis (CZE), and/or dynamic light scattering (DLS) techniques, which may also be referred to as photon correlation spectroscopy (PCS). Other energy interaction techniques may also be used. The term "quasi-elastic" may be used to describe interactions between photons and particles in the spectroscopy techniques described herein because such interactions are not perfectly elastic. That is, when the photon hits the scattering particle, it loses a relatively small amount of energy.

The incident light used in the techniques described herein may be generally coherent. Coherent light is, in general, defined as light, or photons, that all have essentially identical wavelengths that are "in phase." Coherent light may be obtained from lasers. Therefore, incident light is unshifted coherent light used to illuminate the scattering particles. Incoherent light may also be used.

As used herein, scattered light may refer to inelastic (including quasi-elastic) or elastic scattering from a target. Photons generally have wave properties that result from an orthogonal arrangement of an electric field and a magnetic field. In light scattering, as the light encounters the particle, the electric field causes the electrons in the particle to move up and down. The oscillatory movement of the electron causes a secondary field to be established. This field forms the scattered light. Scattered light can include light that results from the oscillatory motion of the electron in the scattering particle that is induced by incident light.

When the photon in the incident light collides with the scattering particle, the photon loses a small amount of energy that results in a slight decrease in the frequency of the incident light. This "phase shift" (also referred to as the Doppler shift) in the scattered light compared to the incident light is the basis for the measurement. The shift in the frequency is detected by mixing the unscattered light with the scattered light on the photo-detector. "Beats" result, and the magnitude of the frequency of the beats is generally proportional to the mobility of the scattering particle. In the case of EQELS, the magnitude of the frequency of the beats is proportional to the electrophoretic mobility of the particle. In contrast, in PCS or QELS, the motion of the particle may be proportional to its diffusion coefficient.

Electrophoretic mobility as used herein refers to motion induced in suspended charged particles that result from the effect of a superimposed electric field and is balanced by the viscous drag of the solvent on the particle. The electrophoretic mobility can be used to calculate size, weight and distributions thereof. It should be understood that the size of a particle is generally equivalent to its diffusion coefficient.

Without wishing to be bound by any particular theory, when the particle is large compared to the Debye Huckle length, the surface charge generally governs the movement of the particle. The Debye Huckle length is defined by the layer of solvent counter ions organized over charged surface of the suspended particle and the thickness of the layer depends on the magnitude of the particle surface charge and the ionic strength of the suspending solution.

The autocorrelation function is a statistical mechanics method for the correlation of the relative positions of a large number of particles (ensemble) and, for example, can have the general form:

$$g^{(2)}(\tau) = <I(t)I(t+\tau)> \quad \text{Eq. 1}$$

Where $\tau$ is the time increment, I is scattered intensity, and t is time. In some embodiments, the time dependence of the auto-correlation function is used to determine the movement over time of an ensemble of scattering particles.

The calculation of the electrophoretic mobility vs. determination of multimer molecular weights may be performed as follows. In some embodiments, the experimental results can be presented in several different formats of quantitative indicia including: (1) the frequency shift, (2) the zeta potential and/or (3) the electrophoretic mobility. The data can also be presented in a form that can include: (1) the diffusion coefficient, (2) the characteristic dimension and/or (3) the molecular weight and/or size. The latter two quantities may be calculated from the diffusion coefficient for each multimer. The diffusion coefficient for each multimer can be determined as follows. If each multimer in the mobility spectra is homogeneous with respect to molecular weight (as it should be by virtue of the electrophoretic technique) then the morphology or the line shape of each band in the spectra should be Lorentzian. A Lorentzian line shape is described as:

$$I_{(S,v)} = \frac{\langle N \rangle S^2 D}{\pi(4\pi^2 v^2 + (S^2 D)^2)} \quad \text{Eq. 2}$$

The ½ width of the individual bands, representing a specific multimer, is $S^2D$, so by plotting the ½ width of each and versus $\sin^2(\theta)D$ can be determined. It will be appreciated that a electrophoretic mobility distribution can thus be determined and/or displayed directly from a calculated and/or displayed electrophoretic mobility distribution, or indirectly from another quantitative indicia as described above.

Embodiments of the present invention provide rapid methods of detecting and analyzing vWF multimers and vWF-metabolic agents such as ADAMTS13. Embodiments of the present invention may be used in the diagnosis of TTP and TTP/HUS, and/or in monitoring of efficacy of the treatment of such conditions. Multimeric vWF species subjected to analysis according to embodiments of the present invention can variously include molecular forms of vWF that differ from one another in molecular weight, molecular conformation, molecular configuration, and/or amino acid sequence.

Embodiments of the present invention are suited to assess vWF multimers suspended in a solution and/or vWF-metabolic agents such as ADAMTS13 in solution, by a variety of techniques, including electrophoretic quasi-elastic light scattering (EQELS),), capillary zone electrophoresis (CZE), and dynamic light scattering (DLS), also referred to as photon correlation spectroscopy (PCS).

Electrophoretic mobility of each vWF multimer can, for example, be determined by electrophoretic quasi elastic light scattering (EQELS), as described below in illustrative embodiments of the present invention.

An exemplary EQELS spectrometer 10 is illustrated in FIG. 1. The spectrometer 10 includes a laser 14 that impinges a beam of light onto a sample 20. The sample 20 is positioned between two electrodes 28 that provide an electric field to the sample 20. Charged particles in the sample 20 are induced to move due to the application of the electric field. For example, the sample 20 can include a sample medium in which particles of interest, such as a vWF sample, are in a solution or suspension. For example, the sample medium can include plasma, plasma products, proteins, nucleic acids, cells, cellular products, polysaccharides and the like. Movement of the particles in the sample 20 is detected by quasi-elastic scattering from the generally coherent light provided by the laser 14. Some of the incident photons can encounter moving particles in the sample 20. When this encounter occurs, a small amount of energy from the photon is given up, and consequently, the frequency of the scattered light is slightly reduced. This scattered light is detected by a detector 26.

As illustrated in FIG. 1, the spectrometer 10 is connected to a processor 12 that includes an EQELS signal analyzer 22. The processor 12 receives signals from the spectrometer 10, which are analyzed by the EQELS signal analyzer 22. For example, the scattered light detected by the detector 26 can be analyzed to determine the magnitude of the small shift in frequency. This shift in frequency is generally proportional to the rate of movement of the particle in the sample 20 and is detected as a Doppler shift. The signal analyzer 22 can measure the Doppler shift through a heterodyne technique in which unshifted light is mixed with the scattered light to produce "beats". This signal is measured as an autocorrelation function that can then be Fourier transformed to yield a power spectrum for interpretation.

In some embodiments, the EQELS spectrometer 10 can be used to detect and/or characterize vWF multimers and/or vWF-metabolic agents, such as ADMTS13 that may be included in the sample 20. Spectra from the EQELS spectrometer 10 may be used to diagnose various conditions, such as the degradation of high molecular weight vWF, TTP, and/or TTP/HUS. Spectra from the EQELS spectrometer may be compared before and after treatment to evaluate the therapeutic value of a given treatment.

In particular embodiments, the EQELS spectrometer 10 is used to detect an EQELS spectrum for a sample 20 that includes vWF multimers in a sample medium. The EQELS spectrum is compared to a database of known spectra, each of the known spectra corresponding to one of a plurality of known vWF conditions, such as healthy vWF or various abnormalities or diseases associated with vWF. The vWF multimers in the medium can be characterized based on the comparison.

In other specific embodiments, the EQELS spectrometer 10 is used to characterize or assess vWF-metabolic agents, such as ADAMTS13.

Figure 2:
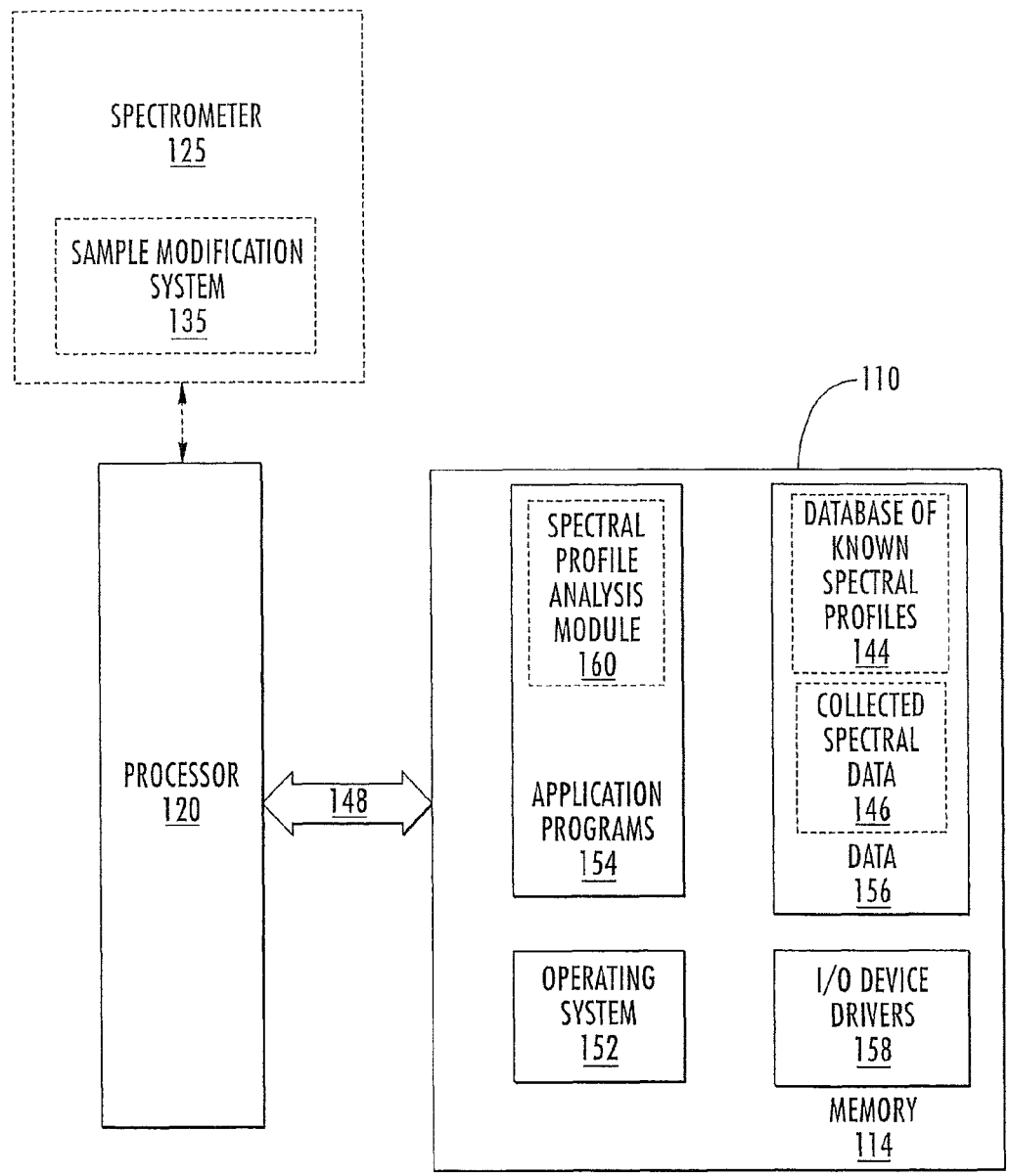
FIG. 2 is a block diagram of data processing systems according to embodiments of the present invention.

FIG. 2 is a block diagram of exemplary embodiments of data processing systems that illustrates systems, methods, and computer program products in accordance with embodiments of the present invention. A data processing system 110 is provided that includes a processor 120 in communication with a spectrometer 125, and a memory 114. Exemplary EQELS systems that can be used for the spectrometer 125 are illustrated in FIG. 1. However, it should be understood that other types of spectrometers may be used, such as PCS, DLS, EQELS spectrometers or CZE devices. As illustrated in FIG. 2, the spectrometer 125 includes a sample modification system 135. The sample modification system 135 is configured to modify the sample in the spectrometer, such as by adding a substance, such as a vWF-metabolic agent (e.g., ADAMTS13) or a therapeutic agent, to the sample.

In some embodiments, the spectrometer 125 and/or the sample modification system 135 is omitted. For example, the sample can be modified manually or a spectrum can be obtained according to embodiments of the invention without modifying the sample with the sample modification system 135. In some embodiments, the spectrometer 125 is omitted and a spectrum obtained from a remote spectrometer is provided to the data processing system 110 for analysis.

The sample modification system 135 can modify the sample, for example, by adding a vWF-metabolic agent such as ADAMST13, adding a solvent, changing the pH of the sample medium, changing the temperature of the sample medium, changing the ionic strength of the sample medium, adding an agent for altering the binding characteristics of a target particle, and/or adding a complexation agent for a target vWF particle. Examples of binders, include antibodies, cells, microbes, ligands, proteins, peptides, nucleic acids, polysaccharides, lipids, lipoproteins, haptens, and pharmaceutical compounds. Sample purification can be accomplished by any of a variety of affinity (immuno- or ligand-) methods. Antibodies or peptides that bind to the sample can be covalently linked to column matrix or to microbeads. The sample can then be bound by the affinity agents and transferred to the desired solution. The sample can then be eluted from the affinity agents and characterized.

The processor 120 communicates with the memory 114 via an address/data bus 148. The processor 120 can be any commercially available or custom microprocessor. The memory 114 is representative of the overall hierarchy of memory devices containing the software and data used to implement the functionality of the data processing system 110. The memory 114 can include, but is not limited to, the following types of devices: cache, ROM, PROM, EPROM, EEPROM, flash memory, SRAM, and DRAM.

As shown in FIG. 2, the memory 114 may include several categories of software and data used in the data processing system 110: the operating system 152; the application programs 154; the input/output (I/O) device drivers 158 and the data 156. The data 156 may include a database of known spectral profiles 144 and/or spectral data 146 from the spectrometer 125. The database of known spectral profiles 144 and/or spectral data 146 can be used to identify or characterize a sample. For example, spectra from vWF samples having a known condition can be used to determine parameters for diagnosis. A spectrum falling within such parameters can then be diagnosed as potentially having the same or a similar condition. For example, certain von Willebrand disease conditions can have a lower concentration of high molecular weigh (HMW) vWF multimers.

As will be appreciated by those of skill in the art, the operating system 152 may be any operating system suitable for use with a data processing system, such as OS/2, AIX, OS/390 or System390 from International Business Machines Corporation, Armonk, N.Y., Windows CE, Windows NT, Windows95, Windows98, Windows2000, or WindowsXP from Microsoft Corporation, Redmond, Wash., Unix or Linux or FreeBSD, Palm OS from Palm, Inc., Mac OS from Apple Computer, LabView or proprietary operating systems. The I/O device drivers 158 typically include software routines accessed through the operating system 152 by the application programs 154 to communicate with devices such as I/O data port(s), data storage 156 and certain components of the memory 114 and/or the spectrometer 125. The application programs 154 are illustrative of the programs that implement the various features of the data processing system 110 and preferably include at least one application which supports operations according to embodiments of the present invention. The data 156 represents the static and dynamic data used by the application programs 154, the operating system 152, the I/O device drivers 158, and other software programs that may reside in the memory 114.

While the present invention is illustrated, for example, with reference to the spectral profile analysis module 160 being an application program in FIG. 2, as will be appreciated by those of skill in the art, other configurations may also be utilized while still benefiting from the teachings of the present invention. For example, the spectral profile analysis module 160 may also be incorporated into the operating system 152, the I/O device drivers 158 or other such logical division of the data processing system 110. Thus, the present invention should not be construed as limited to the configuration of FIG. 2, which is intended to encompass any configuration capable of carrying out the operations described herein.

The I/O data port can be used to transfer information between the data processing system 110 and the spectrometer 125 or another computer system or a network (e.g., the Internet) or to other devices controlled by the processor. These components may be conventional components such as those used in many conventional data processing systems that may be configured in accordance with the present invention to operate as described herein.

Although the present invention is described above with respect to the spectrometer 125, it should be understood that various types of spectrometers and spectrometry techniques may be used, including electrophoretic spectrometers and/or spectrometers in which the sample is not positioned in an electric field. For example, EQELS, PCS or DLS spectrometers may be used for the spectrometer 125. Moreover, other techniques can be used to impinge energy to a sample and to collect an energy interaction output from the sample.

The light-scattering based techniques according to embodiments of the present invention, such as is illustrated in FIGS. 1 and 2, are based on differences in the frequency between light scattered from the moving particle and the incident light impinged on the particle. Since the very small shift in the frequency of the scattered light may not be measured directly, a heterodyne method is used in which the scattered light is mixed with the reference or unshifted light [Johnson, Jr., C S. Laser Light Scattering. Dover Press, N.Y., 1994]. The difference in the frequency between the shifted and unshifted light gives rise to 'beats.' The frequency of beats is related to the magnitude of the frequency shift in the scattered light which is in turn related to the mobility of the scattering particle, e.g., vWF particle. The electrophoretic effect is obtained by superimposing a uniform electric field (which may range from about a few volts/cm to about 30,000 volts/cm) depending on the electrophoretic method used. The field is pulsed and its polarity alternated to avoid sample polarization. The scattered intensity ($I_s$) from a moving particle at a fixed angle ($\theta_s$) is observed as an oscillating intensity in the heterodyne methodolgy as a second order field autocorrelation function $G_{Lhet}^2(\tau)$ [Bern, B J. Dynamic Light Scattering. John Wiley & Son, NY 1976] given by Equation 1:

$$G_{Lhet}^2(\tau) = I_L^2 + 2I_L \langle I_S \rangle \cos(K \cdot v_d \tau) e^{-DK^2 t} \qquad \text{Eq. 3}$$

where $I_L$ is the intensity of the reference beam (local oscillator), and $I_S$ is the intensity of the scattered light, $v_d$ is the velocity of the scattered particle, D is the diffusion coefficient and $\tau$ is the time increment. K is the scattering vector defined by:

$$K = \frac{4\pi n}{\lambda} \sin\left(\frac{\theta_s}{2}\right) \qquad \text{Eq. 4}$$

where n is the refractive index, and $\lambda$ is the wavelength of the incident light. One important quantity in this expression is $K \cdot v_d$, the Doppler shift of the signal resulting from the particle motion. Fourier transform of the measured autocorrelation function gives the power spectrum from which the particle electrophoretic mobilities are calculated [Ware, B R. Electrophoretic light scattering. Adv. Colloid Interface Science 4:1-44, 1974].

Temperature, ionic strength, pH, and conductivity of a sample medium (such as the sample 20 in FIG. 1) may be controlled. Small changes in temperature can be detected by a change in the conductivity, which may be monitored throughout the experiment. Joule heating can be governed by regulation of the pulse duration and the frequency of the electric field. Thermal lensing may be avoided by control of the incident laser power. Electroosmosis can be minimized by coating the scattering cell first with (γ-glycidoxypropyl)-trimethoxysilane, drying at 70° C., coating with methylcellulose, and drying again at 70° C. The absence of electroosmosis artifacts can be verified by a flat electrophoretic profile across the scattering volume. An alternative method is to eliminate the step of coating the cuvette with methyl cellulose and to make mobility measurements at the stationary boundary or use an alternative cell design. Snell's law correction may be made for all scattering angles. The electrokinetic properties of vWF may lie in the area of the Debye-Huckel equation where both surface charge and frictional forces are significant to its movement in an electric field. For example, both the electrical charge and frictional properties of the vWF multimers may contribute to the mobility spectra [Pthica BA. The physical chemistry of cell adhesion. Exp. Cell Res. 8, 123-140, 1961].

Without wishing to be bound by any particular theory, the basis for resolution and distinction between different vWF species using the EQELS technique is generally the difference in the electrophoretic mobility for different vWF multimer species. Electrophoretic mobility is the movement of a charged particle species under the influence of an electric field.

In the absence of an electric field to induce electrophoretic mobility, such as is the case with DLS or PCS techniques (which may be substituted for the EQELS techniques discussed with respect to FIGS. 1 and 2), the species may still undergo movement resulting from thermal effects. The magnitude of such movement, e.g., involving Brownian movement, convective currents and/or diffusional effects, can be determined by solvent conditions, solute concentration, and the molecular size of the scattering particle. Thus, although EQELS may be used to distinguish and resolve differences between vWF multimers and/or determine the number of multimers present, PCS or DLS can also be used to detect vWF multimers based on differences in the diffusion coefficients of the various vWF multimeric species.

PCS thus differs from EQELS in that no electric field is applied across the sample. Differences in the magnitude of movement of the diffusing species are detected from differences in the magnitude of the Doppler shift that result from the interaction of incident photons, such as can be produced by a laser or other light source, and the diffusing species. The rapidly translating or diffusing species can yield a larger Doppler shift and slower diffusing species can yield a smaller Doppler shift. The detection method otherwise corresponds to that employed for EQELS.

PCS can provide an accurate method for determining translational diffusion coefficients for the analysis of vWF multimers. Furthermore, the rapidity with which diffusion coefficients can be measured makes PCS an effective method to monitor macromolecular association. EQELS may be used in the determination of the electrophoretic mobility distribution of the vWF multimers.

By way of illustration, the EQELS technique can be carried out using a sample cell contained in a refractive index matching vat, using toluene as the refractive matching fluid and temperature controlled within a tolerance of 0.1° C. The scattered radiation can be measured by a photo-tube positioned at a defined scattering angle. The z-averaged translational diffusion coefficient may then be obtained from the intensity-normalized photon count autocorrelation function as the slope of the decay constant $\Gamma$ vs. $\sin^2(\theta_s/2)$ where $\Gamma=K^2D$ and K is the scattering vector. The molecular size can be expressed as a hydrodynamic diameter and calculated from D defined by Einstein's equation. Based on exponential sampling techniques, the molecular size distributions (e.g., variation in the size of vWF multimers) can be derived from the PCS autocorrelation function. Von Willebrand factor (vWF) circulates in normal plasma at 10 μg/mL as a polymeric glycoprotein of variable molecular weight ranging from 500,000 to 20 million. The vWF multimers are composed of vWF monomers synthesized in both endothelial cells and megakaryocytes. The 2813 amino acid (360,000 Mr.) nascent vWF monomer, also called the "prepro-vWF monomer," is composed of a 22 amino acid signal peptide, a 741 propeptide (100,000 Mr, 741 amino acids, also called vWF antigen II), and the mature vWF monomer.

The mature monomer contains 2050 amino acids and has a Mr of 260,000. In the endoplasmic reticulum, the negatively charged mature vWF monomers dimerize through a specific disulfide bond arrangement located in the carboxy-terminus. In the Golgi apparatus the resulting dimers in turn polymerize to form vWF multimers through a second set of specific disulfide bonds located in the D3 domain of the monomer. As a result, large polymers are formed. The propeptide is necessary for packing the mature vWF monomer into the Weibel Palade body of endothelial cells and the a-granules of platelets. The propeptide is then cleaved by furin, a subtilisin-like enzyme.

The size of the multimers, and the marked polydispersity of the multimers, can be attributed, at least in part, to proteolysis within the A2 domain by ADAMTS13.

Imaging of the vWF dimer by electron microscopy suggests a structure including two globular domains (26×2.6 nm) connected to a central domain (5 nm) by fibrillar chains (34 nm) giving a total characteristic dimension of about 145 nm). Atomic force microscopy (AFM) of dimeric vWF shows two flanking domains of 73 nm connect to a central domain of 38 nm connected by 5 nm rods. The characteristic dimension for both methods is in good agreement. AFM of globular vWF shows a major axis dimension of 146 nm with unfolded multimers of up to 774 nm. The globular conformation undergoes extension to a linear conformation at a mechanical shear above 35 dynes/cm$^2$. This model is often referred to as a "ball of yarn" and fits well with current concepts of the normal biologic function of vWF. Mechanical shear is highly important in inducing the transformation from the compact "ball of yarn" to the extended state.

Concerning vWF monomer organization, with respect to domain structure and function, the vWF monomer itself is arranged into the following structural domains: $(NH_2)D'$-D3-A1-A2-A3-D4-B1-B2-C1-C2($CO_2H$). The domains are defined as regions of repeating homology. Although not yet fully specified, relationships of biologic functions to domains has been elucidated for some domains.

Concerning the domains D' and D3, one of the important functions of vWF is the transport of coagulation FVIII, which occurs in plasma where vWF is exposed to and binds coagulation FVIII. In addition to this transport function, FVIII while bound to vWF is protected from proteolysis by activated protein C or by activated coagulation factor X (FXa). The binding site has been refined to residues 78-96 in the D'D3 domains of vWF. Non-covalent binding of coagulation FVIII by vWF ($K_d$=0.25 nM) occurs through the interaction of the D' and D3 domains in vWF and the A3 domain in coagulation FVIII, not to be confused with the A3 domain of vWF (81-83). Cleavage of Arg$^{1689}$ in the coagulation FVIII A3 domain releases coagulation FVIII from vWF. Mutations in the coagulation FVIII binding region of vWF at residues 19, 28, 53, 54, and 91 can prevent normal binding of coagulation FVIII to vWF, can cause severe bleeding, may be misdiagnosed as hemophilia, and are referred to as vWF Normandy. The mechanism of coagulation FVIII delivery to the platelet surface has not yet been elucidated.

Concerning domain A1, it is noted that domains A1 and A3 share structural similarities with a large superfamily including I domains of integrins, complement components of extracellular matrix, and dinucleotide binding regions of ras-p21. The positively charged A1 domain is located between amino acid residues 497 and 716 and has a disulfide bridge between Cys 509-Cys 695 producing a rather large loop of 184 amino acids.

Domain A1 together with domains A2 and A3 mediate the interaction between vWF and collagen located in the vascular wall and $GPI_b$/V/IX located on the platelet surface. The A1 repeat contains the binding site for platelet $GPI_b$. $GPI_b$ exists as a complex composed of GP Ib$_\alpha$, GP Ib$_\beta$, GP V and GP IX in a molar ratio of 2:2:1:2, respectively. vWF does not constitutively bind GPI$_b$/V/IX complex, but vWF requires activation through extension of the molecule.

The binding of GPI$_b$ by the A1 domain is thought to involve a conformational change in the A1 domain that may be modulated by the interaction between domain A3 and non-fibrillar collagen. The exact details of the conformational change are not known. According to analysis of the A1 domain crystal structure and by analogy with data from the α-subunits of leukocyte integrins (αM β2 and α$_L$β2, also referred to as I domains), it has been postulated that disruption of buried salt bridges may lead to a charge redistribution and displacement of the α7 helix 10A downward from the upper front surface as in the I domain of integrins. In the case of the I domain, this distended shape is associated with high affinity ligand binding and presumably this extended shape in vWF A1 is associated with GP I$_b$ binding. It is thought that the interaction of the A3 domain with collagen and/or high mechanical shear initiates this conformational change. The A1 domain also contains a secondary binding site for collagen type VI, and binding sites for sulfatides, aurin tricarboxylic acid (ATA), Botrocetin and heparin.

The A2 domain is defined by the amino acid region 717 to 909. This vWF domain contains a site between Tyr 842 and Met 843 that is cleaved by plasma ADAMTS13 and is thought to be responsible for the regulation of the vWF multimer size. After cleavage by ADAMTS13, the vWF dimer is reduced to two fragments with masses of 176 K$_d$ and 140 K$_d$. ADAMTS13, which requires either calcium or zinc for activity, does not attack vWF unless vWF is unfolded and extended as it would be by either mechanical shear or after interaction with collagen or other proteins. Deletion of the A2-domain prevents multimer cleavage.

The negatively charged A3 domain extends from amino acids 910 to 1111. This domain contains the binding site for type I and type III collagen and is located between amino acids 1018 to 1114. The binding sites for type IV and VI collagen are not known, and do not appear to be in either the A1 or the A3 domains. Based on isolated recombinant A-domains, including chimeric domains composed of parts of A1 and A3, and on vWF molecules with either A1 or A3 deleted, the major collagen binding site has been located to the A3 domain. Isolated recombinant A3 domains bind to type I collagen with a K$_d$ of 1.8×10$^{-6}$ M.

The mechanism of collagen binding and vWF-mediated platelet adhesion is complex, involves multiple steps, and varies with the collagen type. In contrast to I domains found in leukocyte integrins (LFA-1), no metal binding site is present in either the A1 or A3 domains of vWF. The motif of the dinucleotide binding fold, characteristic of the I domains and formed by a central parallel β-sheet flanked by two amphiphilic helices, is present in the vWF A-domains and is postulated to be the binding sites for GP I$_b$ and collagen respectively. The A-domains and the A3-domain in particular, may contain the hydrophobic regions that are empirically observed.

vWF has two major functions, initial platelet adhesion and coagulant FVIII transport to platelets. A variety of collagens located in the subendothelial basement membrane and the vascular periadvential tissue have been identified as specific targets for vWF, but the fibrillar collagens, types I and III, the microfibrillar collagen type VI, and the non-fibrillar collagen type IV are the most important. High mechanical shear physically distorts vWF into an elongated molecule enhancing its function in platelet adhesion. While the importance of mechanical shear in activating vWF has been challenged, the importance of collagen binding has been reinforced by baboon studies showing that inhibition of collagen binding by blocking the A3-domain with a monoclonal antibody prevents in vivo arterial platelet thrombus formation.

Initial interaction between collagen, vWF, and platelets serves only as an initial step in platelet adhesion. Other ligands, perhaps $\alpha_2\beta_1$, appear to be responsible for tight adhesion. Under high shear, subendothelial vWF may account for up to 50% of platelet adhesion.

Collagen binding by the A3-domain appears to induce a conformational change in the A1-domain to expose a region that then binds to the constitutively present glycoprotein IbN/IX (GPI$_b$/V/IX) on the platelet surface. The major binding site for GPI$_b$ resides in vWF residues 514-542 since this sequence will inhibit binding of asialo-vWF, vWF-platelet aggregation, and binding of both ristocetin and Botrocetin. vWF binding of ristocetin or Botrocetin enhances vWF binding to GPI$_b$/V/IX, but negatively charged or aromatic polymers inhibit binding to GPI$_b$. When GPI$_b$ binds vWF, signal transduction is induced and platelet activation results. Platelet activation is followed by vWF or fibrinogen binding to $\alpha_{IIb}\beta_3$ that mediates platelet spreading, aggregation, irreversible platelet adhesion and thrombin production. Under high shear conditions platelet aggregation is mediated through vWF binding to $\alpha_{IIb}\beta_3$.

Abnormalities in the distribution of vWF multimer size and concentration can arise from congenital or acquired causes. Losses of HMW multimers are especially significant since HMW multimers are the principle mediators of platelet adhesion. Type I vWD is the most common type of vWD and has a decrease in the concentration of all multimer sizes. In type II vWD, the HMW multimers are decreased or absent. In Type IIB vWD the vWF multimer has a decreased affinity for GPI$_b$/V/IX complex, which may result from mutations in the A1-domain that increase vWF vulnerability to proteolysis. Mutations predominantly in the A2-domain lead to Type IIA vWD where cleavage between residues Tyr842-Met843 degrades vWF and results in loss of HMW vWF multimers. Molecular size and weight distributions, electrophoretic mobility distributions, and/or size distributions of vWF in a sample as determined, for example, using the spectral techniques described herein may be used to identify these and other conditions.

Concerning clinical disease states associated with vWF, Von Willebrand Disease is a clinically heterogeneous disease with a number of disease variants, each characterized by different quantitative and/or qualitative defects in vWF. There are three major disease types: (Type I, II, III) and four subtypes (IIA, IIB, IIM, IID). The laboratory diagnosis and subtyping of vWD has been challenging since vWD does not appear on routine diagnostic blood tests. Physicians therefore must order specialized diagnostic blood tests to determine the specific vWD variant in order to establish the best and safest treatment for each patient, as noted hereinearlier.

Thrombotic thrombocytopenic purpura (TTP) and hemolytic uremic syndrome (HUS) are disease states involving vWF multimer distribution and ADAMTS13 activity. Thrombotic thrombocytopenic purpura (TTP) is a rare and potentially fatal illness more common in young adults and females. The diagnosis of TTP is defined by the classic pentad of fever, renal failure, fluctuating mental status, microangiopathic hemolytic anemia (MAHA), and thrombocytopenia. The related hemolytic uremic syndrome (HUS) is more often seen in children infected with *E. Coli* 0157:H7 and presents with greater renal dysfunction and less nervous system involvement. Both congenital and acquired forms of the disease exist. Acquired TTP may arise from many different clinical settings including, infection (especially Shiga-toxin from E. coli 0157:H7 or AIDS), autoimmune diseases such as SLE, bone marrow transplant (BMT), pregnancy, chronic immune suppression, sepsis, and drugs such as ticlopidine, cyclosporine, mitomycin C, and quinine.

Thus, TTP is a syndrome of diverse etiologies that is fatal>80% of cases without plasma exchange transfusion (PLEX). Even with PLEX, mortality rates in 15% to 20% range are still common. The effect of PLEX is thought to involve replacement of the missing vWF cleavage protease (vWFCP) through infusion of normal plasma and, in some cases, removal of inhibiting autoantibody such as IgG immunoglobulin. The observation that chronic relapsing TTP was associated with ultra large vWF multimers (ULvWF) suggests that a "depolymerase" regulating multimer size may be absent in TTP, since these ULvWF multimers are more readily bound to platelets. Plasma protease (vWFCP) is effective to cleave vWF and in TTP, vWF is cleaved in the A2-domain of vWF between $Tyr^{1605}$-$Met^{1606}$. Cleavage of vWF by vWFCP is facilitated by shear-extension of vWF.

Patients with congenital TTP have been shown to have mutations in ADAMTS13. Members of the ADAM (a disintegrin and metalloproteinase) family play a prominent role in metabolism of extracellular matrix adhesive proteins. The ADAMTS family has the addition of thrombospondin-1 repeats that presumably function in collagen binding. The function of members of the ADAMTS family is very diverse, but all family members are membrane-anchored proteases that process extracellular matrix adhesive glycoproteins. ADAMTS13 mediates cleavage of vWF, with obvious implications for TIP. The proteolytic action may involve activation of vWFCP and/or other components of hemostasis.

Inheritance of ADAMTS13 is autosomal recessive. ADAMTS13 is a 1427 amino acid residue glycoprotein that consist of a signal peptide, a 41aa propeptide, a reprolysin-like domain, a metalloproteinase domain, a disintegrin-like domain, a thrombospondin-1 repeat, Cys-rich spacer domains that contain RDG sequences, followed by 7 additional thrombospondin-1 domains and 2 CUB-domains. The calculated Mr of 154 k (nonglysolated) agrees well with 190k $M_r$ (glysolated) vWFCP isolated from plasma. ADAMTS13 is distinguished from other members of the ADAMTS family by its short propeptide, only 41 residues long, and the presence of CUB-domains. The CUB domains are unique to ADAMTS13 and contain collagen binding sites. Cellular matrix binding is postulated to result from the thrombospondin domains. The nascent protein is though to be a zymogen that requires activation either in the Golgi or at the cell surface, possibly by furin. The $t_{1/2}$ for ADAMTS13 contained in infused plasma after PLEX is not known with certainty, but has been measured at 3.3 days and 2.1 days in two patients with TTP who were being PLEX'ed. Depression of the functional activity to <3% appears to be required to express clinical significance. The association of either a functional or congenital deficit of ADAMTS13 with congenital and idiopathic TTP appears firmly established for approximately 50% of patients with TTP.

Low levels of ADAMTS13 and HMW multimers are also present in disease states and physiological conditions other than TTP, such as VOD, acute pancreatitis, pregnancy, uremia, essential thrombocytosis, inflammation and cirrhosis. While the invention is described with reference to TTP, HUS, and TTP/HUS in specific embodiments of the invention, it will be appreciated that such disease states are illustrative in character as regards the applicability of the invention, and that the invention encompasses applications including the diagnosis, treatment, and/or amelioration of symptoms of a variety of disease states and physiological conditions involving anomalous production of vWF, eg., disease states in which abnormal endothelium function mediates release of vWF, such as for example acute coronary syndrome. The assay methods of the present invention correspondingly encompass applications in which the potential presence of these disease states and/or physiological conditions is diagnostically determined or contraindicated.

The present invention therefore provides a rapid assay method for the detection and characterization of vWF multimers and/or degradation of vWF by agents such as ADAMTS13 having utility in connection with diagnosis and treatment of disease states and/or physiological conditions that are associated with, indicated or contraindicated by, or otherwise involve vWF and/or degradative agents thereof.

The rapid assay methods of the invention include, without limitation, methods utilizing static light scattering methods and dynamic light scattering methods including EQELS (Electophoretic Quasi Elastic Light Scattering, PCS (Photon Correlation Spectroscopy) and the like or CZE (Capillary Zone Electrophoresis) techniques, or other methods for detecting and/or characterizing vWF and/or degradative agents thereof, by impinging energy on a medium containing or susceptible to presence of vWF species and/or degrative agents thereof, to generate an energy interaction spectrum, and determining the presence, absence or character of such species and/or agents from the energy interaction spectrum.

The energy interaction spectrum generally can be of any suitable type, including energy scattering spectra, energy absorbance spectra, energy transmittance spectra, or any other spectrum indicative of the energy/particle interaction involving such species and/or agents. The energy interaction may be conducted under electrophoretic or non-electrophoretic conditions, and the energy source can be of any suitable type effective to generate the desired interaction spectrum, including, without limitation, electromagnetic energy, acoustic energy, ultrasonic energy, or any other suitable energetic medium. In the case of electromagnetic energy, the energy can be of appropriate spectral regime, such as visible light, infrared, ultraviolet, and x-ray spectral regimes. In specific embodiments, actinic radiation is employed as the energetic medium for interaction with the vWF and/or metabolic agent (e.g., ADAMTS13) particle in the sample, and such radiation can for example have a wavelength in a range of from about 200 nm to about 700 nm. Various embodiments of the invention employ visible light radiation, such as light-scattering techniques including elastic light scattering and quasi-elastic light scattering. Other embodiments employ uv radiation, such as capillary electrophoresis methods and systems having a uv laser as an energy source for uv radiation impinged on the particles in the capillary flow stream. It will therefore be recognized that any suitable energy detection source and corresponding energy medium can be employed in the broad practice of the invention. In various preferred embodiments, a visible light laser is utilized as the energy detection source, for conducting static light scattering methods and dynamic light scattering methods including EQELS (Electophoretic Quasi Elastic Light Scattering, PCS (Photon Correlation Spectroscopy) and the like or CZE (Capillary Zone Electrophoresis) techniques.

The determination (e.g., detections, characterizations) of the vWF species and/or associated agents, from the energy interaction spectra may be made in a suitable manner, using any appropriate software, systems, analytical techniques, algorithms, etc. for such determination. Illustrative determination methods, discussed with primary reference to EQELS as illustrative of energy interaction spectral approaches, are described, for example, in copending U.S. patent application Ser. No. (unassigned) filed May 4, 2004, entitled, "Electrophoretic Interactive Spectral Methods and Systems for the Detection and/or Characterization of Cells and/or Microbes", the contents of which is hereby incorporated herein by reference.

Subjects can be identified who are at risk of developing TTP disease or any other disease states that causes abnormal function of the endothelium to release vWF or physiological conditions associated with an absence or deficiency of ADAMTS13 and/or any metabolic agents correlative to the presence, absence or character of vWF species in a physiological sample derived from such a subject. The presence, absence or character (e.g., as determined by spectral analysis) of vWF species in the physiological sample can be determined. The absence or deficiency of ADAMTS13 and/or any metabolic agent of vWF can be correlatively determined.

A patient with TPP disease or any other disease states that causes abnormal function of the endothelium to release vWF or physiological conditions associated with an absence or deficiency of ADAMTS13 and/or any metabolic agent of vWF can be treated. A therapeutic agent combating the absence or deficiency of ADAMTS13 can be administered to such a patient, and the effect of the therapeutic agent can be determined by the presence, absence or character of vWF species in a physiological sample derived from the patient after administration of the therapeutic agent. The presence, absence or character of the vWF species in the physiological sample is determined in various specific embodiments by static light scattering methods and dynamic light scattering methods including EQELS (Electophoretic Quasi Elastic Light Scattering, PCS (Photon Correlation Spectroscopy) and the like or CZE (Capillary Zone Electrophoresis) or other energy interaction spectral techniques.

Treatment of a patient with TPP disease or any other disease states that causes abnormal function of the endothelium to release vWF or physiological conditions associated with an absence or deficiency of ADAMTS13 and/or any metabolic agent of vWF, may include administering a therapeutically effective amount of an ADAMTS13 protease, such as a protease selected from: recombinant ADAMTS13; synthetic ADAMTS13; mutants, variants, fragments and fusions of recombinant ADAMTS13; and mutants, variants, fragments and fusions of synthetic ADAMTS13, as more fully described in U.S. Patent Publication No. 2003/0073116 published Apr. 17, 2003, the contents of which is hereby incorporated herein by reference.

The electrophoretic mobility and size distribution of vWF multimers can be analyzed. A medium can be provided including a plurality of vWF multimers therein. Energy can be impinged on the vWF multimers in the sample medium, and an energy interaction output can be generated responsive to the impinged energy. The electrophoretic mobility and size distribution of vWF multimers in the medium can be determined from the energy interaction output.

The energy can for example include light energy, and the energy interaction output can correspondingly include a scattered light output. The energy interaction can be under electrophoretic or non-electrophoretic conditions, as may be desired in a given end use application of such method. Such scattered light output can be processed to determine phase shift of the scattered light from an autocorrelation function, doppler shift of the scattered light in relation to incident light impinged on the vWF multimers, mobility (electrophoretic mobility in the case of electrophoretic conditions being imposed) of the vWF multimers, and the molecular weight distribution of the vWF multimers. The normal range of vWF multimer weights is in a range of from 500,000 to 20,000,000, with weights of from 10 to 20 million generally being considered high, and with ultra large multimer weights being greater than 20 million, and in some instances as high as 100 million.

The scattered light output processing steps can be conducted in a very rapid manner, such as less than 5 minutes, less than 1 minute or even less. The sample can be held in a chamber, which may, for example, be the electrophoretic cell of an EQELS apparatus, or the capillary chamber of an CZE system.

The medium containing the vWF multimers can for example include a buffered dilute salt solution, patient plasma, purified (e.g., chromatographically purified) plasma, or other physiological fluid or reagent solution.

vWF from either normal or processed plasma may be further purified using one of a variety of different methods that include gel permeation chromatography or an affinity method. The affinity method could be immunoprecipitation or immunoaffinity using antibodies, peptides (collagen fragments, and the like) or carbohydrates (i.e. heparin and the like) directed to specific binding sites on vWF that are attached to chromatography matrix, microparticles, or the like. vWF bound to the substrate may be washed with an appropriate buffer to remove undesirable substances, recovered from the wash buffer and then re-suspended in an appropriate elution buffer. The microparticles may be removed and the vWF-containing supernatant recovered. The vWF solution may then be de-salted and exchanged into the assay buffer.

vWF-metabolic enzymes (e.g., ADAMTS13) can be characterized in a patient sample, e.g., a plasma sample from the patient. An amount of high molecular weight vWF can be introduced to the patient sample. Energy can be impinged on the patient sample to which high molecular weight vWF has been added. An energy interaction output can be generated, and whether degradation of the high molecular weight vWF has occurred can be determined from the energy interaction output.

The impingement of the energy on the HMW vWF-augmented patient sample and responsive generation of an energy interaction output, can include static light scattering methods and dynamic light scattering methods including EQELS (Electophoretic Quasi Elastic Light Scattering, PCS (Photon Correlation Spectroscopy) and the like or CZE (Capillary Zone Electrophoresis)or other energy interaction spectral techniques.

The method of characterizing the patient sample for the vWF-metabolic enzyme may further include a determination, if degradation has occurred, of the presence of the unique 176,000 Mr degradation fragment, as a verification marker for the degradation by ADAMTS13. Since this degradation fragment is specific for ADAMTS13, a mobility corresponding to such fragment will grow as degradation of HMW vWF by ADAMTS13 proceeds.

If no degradation of the HMW vWF is determined to have occurred, such a result is indicative that the patient from whom the patient sample was derived lacks the ADAMTS13 enzyme.

The above-described method of characterizing vWF-metabolic enzyme, such as ADAMTS13, can be used to assess in a patient sample treatment efficacy of therapeutic agents and/or treatment regimens.

The electrophoretic mobility distribution and/or size distribution of vWF multimers in a liquid medium can be determined. Energy can be impinged on the medium to generate an energy interaction output. The energy interaction output can be used to determine the presence, absence, or electrophoretic mobility distribution character of the vWF multimers in the medium.

The energy impingement and energy interaction output determination technique can be a technique such as static light scattering methods and dynamic light scattering methods including EQELS (Electophoretic Quasi Elastic Light Scattering, PCS (Photon Correlation Spectroscopy) and the like or CZE (Capillary Zone Electrophoresis). A determination of the presence or absence of vWF multimers in the medium can be made based on the spectral analysis. For example, the spectrum can be compared to known spectra having a particular condition or analyzed for characteristics that may be expected in a particular condition, such as high molecular weight vWF in a patient having a vWF-metabolic enzyme deficiency. The medium itself may include plasma or plasma components, and/or dilute buffer salt solution, other reagents, other physiological specimens, etc. The medium can include (i) a plasma sample derived from a subject, and (ii) a predetermined amount of high molecular weight vWF. The vWF-metabolic enzymes in the subject can be analyzed based on the amount of degradation of the high molecular weigh vWF in the sample as determined based on electrophoretic mobility distributions and/or size distribution.

The characteristics of vWF multimers in the medium attributable to presence or absence of vWF-metabolicenzyme in a plasma sample derived from a subject can be determined. The vWF-metabolic enzyme can include ADAMTS13, and the characteristics of vWF multimers in the medium attributable to presence or absence of the vWF-metabolic enzyme can be determined as the presence or absence of a vWF metabolic product fragment having a molecular weight of 176,000 Mr.

A diagnosis for a subject can be determined from the presence or absence of the vWF-metabolic enzyme in the plasma sample derived from the subject. For example, a diagnosis can be established from the presence or absence of the vWF metabolic product fragment having a molecular weight of 176,000 Mr. Alternatively, the diagnosis can be a conclusion as to the presence of or absence of or susceptibility to a physiological condition associated with a deficiency of the vWF-metabolic enzyme in the plasma sample derived from the subject, e.g., a conclusion of presence of or absence of or susceptibility to a physiological condition associated with a deficiency of ADAMTS13 in the plasma sample derived from the subject.

The assay methods may, in specific embodiments, be carried out in conjunction with administering to a subject a therapeutic agent that is actually effective or is a candidate identified as potentially effective to increase presence of the vWF-degradative enzyme in the subject. Such administration of therapeutic agent may be conducted before and/or after the determination is made by the assay, so that the efficacy of the administration is determinable. The therapeutic agent can be of any suitable type, e.g., an ADAMTS13 protease selected from the group consisting of: recombinant ADAMTS13; synthetic ADAMTS13; mutants, variants, fragments and fusions of recombinant ADAMTS13; and mutants, variants, fragments and fusions of synthetic ADAMTS13. The therapeutic agent can also include candidate therapeutic agents that are to be assessed as to their effectiveness in increasing the presence of the vWF-metabolic enzyme in the subject. In such instance, the assay determination can be conducted to determine the effectiveness of the candidate agent to increase presence of the vWF-metabolic enzyme, e.g., ADAMTS13, in the subject in relation to effectiveness of other candidate therapeutic agents.

A subject can be identified as having or being at risk of developing a disease state or physiological condition associated with an absence or deficiency of ADAMTS13 and/or any metabolic enzyme of vWF. A physiological sample of a type in which ADAMTS13 is present in a normal subject can be obtained from the subject. A predetermined amount of HMW vWF can be added to the physiological sample. The physiological sample to which the predetermined amount of HMW vWF has been added can be processed by processing such as static light scattering methods and dynamic light scattering methods including EQELS (Electrophoretic Quasi Elastic Light Scattering, PCS (Photon Correlation Spectroscopy) and the like or CZE (Capillary Zone Electrophoresis), to determine electrophoretic mobility and size distribution of vWF multimers therein attributable to metabolism of the HMW vWF by ADAMTS13. The subject then is identified as having or being at risk of developing a disease state or physiological condition associated with an absence or deficiency of ADAMTS13 and/or any metabolic agents of vWF based on the electrophoretic mobility and size distribution of vWF multimers.

The physiological sample can include plasma, or plasma after purification (e.g., by chromatographic purification). The physiological sample can further include a reagent that can (i) bind to the HMW vWF and/or vWF multimers attributable to metabolism of the HMW vWF by ADAMTS13 and/or any metabolic agents of vWF and/or (ii) alter mobility characteristics of the HMW vWF and/or vWF multimers when bound thereto for enhanced EQELS determination of the electrophoretic mobility distribution. Botricetin is illustrative of such reagents.

The foregoing methods can be conducted to determine the electrophoretic mobility distribution of vWF multimers, as including or not including a vWF fragment having a molecular weight of 176,000 Mr, attributable to proteolytic action of ADAMTS13 on the high molecular weight vWF.

When EQELS is used, light can be impinged on the physiological sample to produce a scattered light output. The scattered light output can be processed to determine (i) phase shift and doppler shift of scattered light in the scattered light output, relative to the impinging light, and (ii) mobility of vWF multimers produced by degradation of HMW vWF by ADAMTS13.

The foregoing method is useful for diagnosis of TTP, HUS TTP/HUS, and any diseased state that causes abnormal function of endothelium to release vWF, such as Acute Coronary Syndrome, Diabetes, Hypertension, Menorraghia, Renal failure, etc.

A patient with a disease state or physiological condition associated with an absence or deficiency of an enzyme effective to metabolize vWF, e.g., TTP, HUS and TTP/HUS can be treated and/or the effectiveness of the treatment can be assessed. A patient can be administered a therapeutic agent for combating the absence or deficiency of the enzyme. A physiological sample of a type in which the enzyme is present in a normal subject can be obtained. A predetermined amount of HMW vWF is added to the physiological sample, which then is processed, such as by static light scattering methods and/or dynamic light scattering methods including EQELS (Electrophoretic Quasi Elastic Light Scattering, PCS (Photon Correlation Spectroscopy) and the like or CZE (Capillary Zone Electrophoresis), to determine electrophoretic mobility and size distribution of vWF multimers therein attributable to metabolism of the HMW vWF by the enzyme. The efficacy or non-efficacy of the therapeutic agent may then be determined based on the electrophoretic mobility and size distribution of vWF multimers.

Such treatment method can include processing to determine electrophoretic mobility and size distribution of vWF multimers, as including or not including a vWF fragment having a molecular weight of 176,000 Mr.

The treatment method can otherwise include similar aspects, e.g., in respect of the physiological sample, disease states and physiological conditions, etc., as described for the diagnostic method described hereinabove. The enzyme may include ADAMTS13, and the therapeutic agent may include an agent effective for increasing the amount of the enzyme in the patient.

Systems for carrying out the various operations discussed herein, such as the systems illustrated in FIGS. 1 and 2, may also be provided.

Systems for identifying a subject as having or being at risk of developing a disease state or physiological condition associated with an absence or deficiency of an enzyme mediating degradation of vWF can include a means for obtaining from the subject a physiological sample of a type in which the enzyme is present in a normal subject, as well as means for adding to the physiological sample a predetermined amount of HMW vWF. These means may include a container or vial in which the physiological sample is collected, and a container or vial containing a specific amount of HMW vWF. Samples may be obtained from venipuncture, tissue biopsy, tissue culture, cellular contents, recombinant processes and the like.

The system further includes a sample processor arranged to process the physiological sample to which the predetermined amount of HMW vWF has been added. The sample processor includes a static light scattering and/or dynamic light scattering spectrometer, such as spectrometers that may employ EQELS (Electophoretic Quasi Elastic Light Scattering, PCS (Photon Correlation Spectroscopy) and the like or CZE (Capillary Zone Electrophoresis) The resulting spectrum can be analyzed, for example, using automated software to (i) determine electrophoretic mobility and size distribution of vWF multimers attributable to metabolism of the HMW vWF by the enzyme; and/or to (ii) produce a correlative output useful for identifying the subject as having or being at risk of developing a disease state or physiological condition associated with an absence or deficiency of the enzyme, based on the electrophoretic mobility and size distribution of vWF multimers.

The static light scattering methods and dynamic light scattering techniques described herein, such as EQELS, PCS and the like, or CZE, may be commercially available processor apparatus, whose structure and operation may be readily adaptable to the practice of various aspects or embodiments of the present invention. Any suitable hardware and software components and assemblies, e.g., as described with respect to FIG. 2, including general purpose programmable computer systems, microprocessors, registers, storage, output displays and terminals, etc., can be operatively arranged to conduct the electrophoretic mobility and/or size distribution analysis described herein, and/or to provide an output based on such electrophoretic mobility distribution determinations.

The invention in other embodiments relates to an assay kit for rapid determination of an absence or deficiency of an enzyme mediating degradation of vWF in a subject. The kit includes collecting from a subject a predetermined amount of a physiological sample of a type in which the enzyme is present in a normal subject. The kit also includes a predetermined amount of HMW vWF for addition to the predetermined amount of the physiological sample, to provide an analysis sample for static light scattering methods and dynamic light scattering methods including EQELS (Electophoretic Quasi Elastic Light Scattering, PCS (Photon Correlation Spectroscopy) and the like or CZE (Capillary Zone Electrophoresisanalysis of electrophoretic mobility and size distribution of vWF multimers therein attributable to metabolism of the HMW vWF by the enzyme, whereby an absence or deficiency of the enzyme in the subject is determinable. The kit may also be used to obtain a vWF multimer distribution and/or to detect collagen binding, vWF antigens, FVIII binding, etc.

The physiological specimen can be collected by any suitable means, such as a container, vial, or other vessel for receiving and storing the physiological specimen until it is used in the assay procedure. The predetermined amount of HMW vWF may be provided in a second container or vial, from which the high molecular weight vWF can be introduced into the container or vial holding the physiological specimen (or vice versa).

The assay kit can also include written instructions for conducting the rapid determination, and/or a reagent (i) binding to the HMW vWF and/or vWF multimers attributable to metabolism of the HMW vWF by the enzyme and (ii) altering mobility characteristics of the HMW vWF and/or vWF multimers when bound thereto. Botricetin is illustrative of such reagents.

In some embodiments of the present invention, a purified vWF multimer districution assay is used. Minimum amounts of sample may be required for vWF structural analysis, for example, less than about $10\mu$. The assay can be carried out with initial vWF purification from human plasma obtained by centrifugation of whole blood collected into an acid-citrate-dextrose (ACD) vial. Patient plasma may be applied to a CL-4B chromatography column and the void volume containing the vWF can be collected. Alternatively, immunoaffinity microbeads may be used to adsorb vWF and the vWF may be eluted from the beads. High molecular weight (HMW) vWF multimers appear in the leading portion of the void volume followed by lower molecular weight (LMW) vWF multimers in the trailing portion. The vWF fractions are collected, pooled, and analyzed. The final working buffer can for example comprise 40 mM NaCl, 6.5 mM Tris, and 5 mM sodium citrate, at a pH of 7.4, but it will be appreciated that the composition, concentrations and pH of the buffer solution can be varied widely in the general practice of such technique. The working solutions are further diluted with the working buffer yield the final desired vWF concentration, e.g., in the range of from 5 to about 20 µg vWF/ml of solution.

As an alternative approach for avoiding the necessity of initial purification of vWF from plasma, the plasma vWF multimer distribution assay involves addition of a reagent that specifically binds vWF in a manner that uniquely modifies the mobilities of the vWF multimers so that they can be distinguished from other plasma proteins, such as albumin, immunoglobulins and fibrinogen, that are present in high concentrations. vWF mobility modification agents potentially useful in particular embodiments of such assay technique include Botrocetin, anturin tricarbolic acid, collagen, heparin, and monoclonal antibodies that bind to vWF multimers in a manner effective for such mobility modification.

Figure 3:
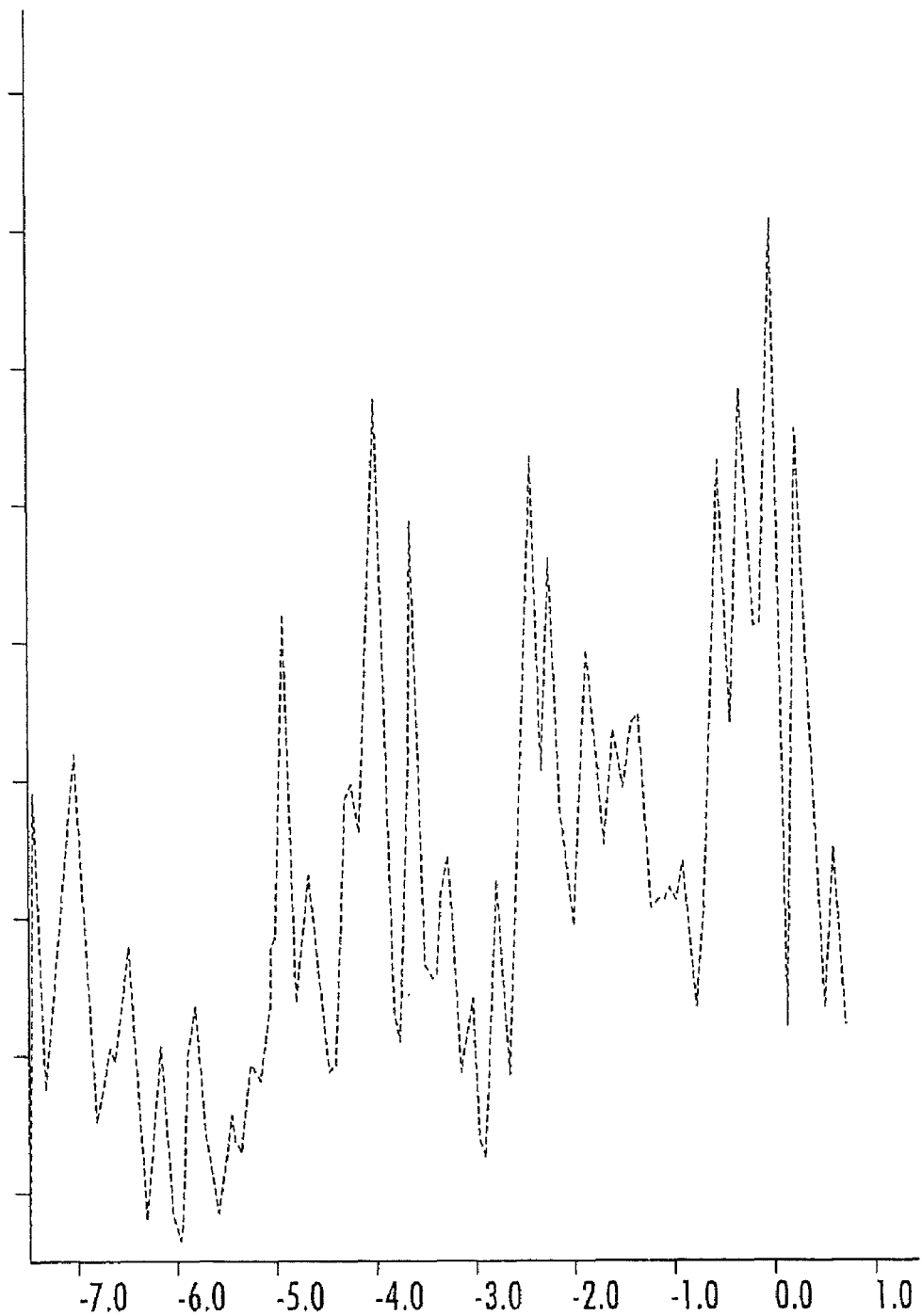
FIG. 3 is a plot of electrophoretic spectrum results of an EQELS experiment involving normal vWF under non-denaturing conditions, wherein relative intensity of each vWF multimer in the sample is shown as a function of multimer mobility, in units of (μ-cm)/(volt-sec), and with an inset of a Western Blot electrophoresis gel of the same vWF sample, for purposes of comparison.

FIG. 3 shows the results of an electrophoretic quasi-elastic light scattering spectrum of normal vWF under non-denaturing conditions. The vWF concentration was 20 µg/mL and the spectrum acquisition time was 20 seconds. The abscissa shows the mobility of vWF multimers in standard units of $(\mu\text{-cm})/(\text{volt-sec})$. The ordinate shows the relative intensity of each vWF multimer. The relative intensity is determined by both the concentration of the vWF multimer and the heterodyne ratio, which is the efficiency of the mixing of the scattered and unscattered light. The concentration of each multimer can be determined from the product of the total concentration of vWF in the sample and the ratio of the total area under the scattering envelope to area under the curve for the specific multimer. Heterogeneity of each multimer band can be assessed from a plot of the band width at half height versus K. Furthermore, an increase in the number of bands corresponding to individual multimers is shown in relation to the reduced number of vWF multimer bands observed using Western Blot electrophoresis gel (shown in the inset of FIG. 3).

An advantage of various embodiments of the assay methodologies of the invention is that they do not require preliminary assumptions to obtain information on the shape, size, and molecular weight of macromolecules as compared to conventional assays.

An electrophoretic spectrum of vWF can be obtained to provide a multi-band spectrum as a result of the polydispersed nature of vWF multimers. The multiple bands that generally correspond to vWF multimers of different sizes can be reduced to one major band by the depolymerization of vWF multimers using dithiothreitol to lyse the disulfide bonds connecting the constituent monomers that form the vWF multimers.

Figure 4A:
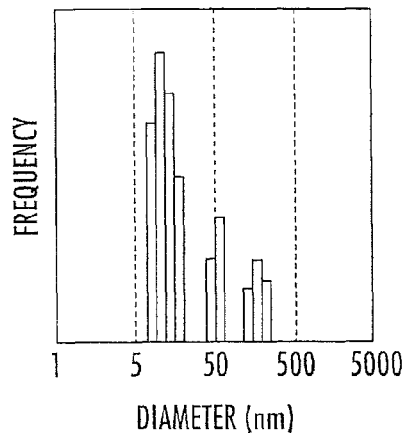
FIGS. 4a and 4b are plots of z-averaged particle size distribution of vWF multimers, in which particle size is plotted as a function of the number of multimers of such size in the sample.
Figure 4B:
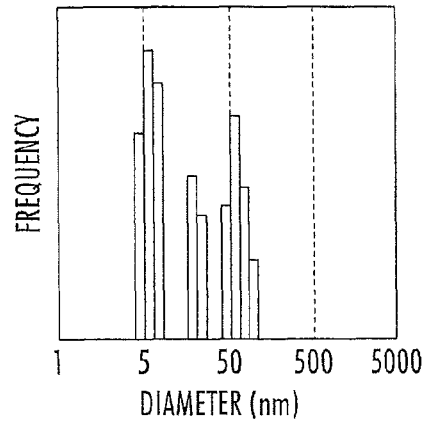

FIG. 4a and FIG. 4b show the z-averaged particle diameter distribution, i.e., the particle size plotted against the number of multimers of that specific size present in the sample. Z-averages are preferred for average size parameterization in the practice of the invention because they strongly emphasizes high molecular weight species, thereby dramatically improving the resolution and providing physical details of the largest vWF multimeric forms.

It will be appreciated that the vWF characterization methods of the present invention can be usefully employed to determine molecular properties of vWF by effects of ionic strength, pH, temperature, and hydrophobicity.

The invention in other embodiments provides an assay, viz., an ADAMTS13 Electrophoretic Quasi-Elastic Light Scattering Assay, to determine the presence, activity, and concentration of ADAMTS13 in a sample. In one such embodiment, high molecular weight vWF (HMW vWF) multimers are isolated and characterized with respect to function, molecular, and concentration. The patient sample then is mixed with the standard HMW vWF. If no degradation of the normal HMW vWF occurs, then the test indicates that the patient is deficient in ADAMTS13. This assay is then repeated with normal standard plasma. In this manner a percent of deficiency compared to normal ADAMTS13 levels is calculated. In addition to degradative loss of the HMW vWF multimers, the assay also permits observation of the presense of the unique vWF degradation fragment of 176,000 Mr as a further marker for confirmation of the results.

In general, a small amount of a standard high molecular weight vWF is added to a small amount of patient plasma. The sample is then examined to determine if the vWF is degraded and, if degradation did occur, that the unique vWF fragment (176,000) is produced. A mobility corresponding to this fragment grows as the degradation by ADAMTS13 proceeds. If no degradation occurs, the result indicates that the patient lacks the enzyme. This assay is highly valuable for a number of applications, including following treatment of TTP/HUS, make the diagnosis of TTP/HUS, etc.

The invention in a further embodiment provides a Collagen Binding Assay using ELS. In this assay, vWF is isolated from the patient using a gel permeation chromatography isolation technique. Standard collagen types, e.g., Types I, III, IV, and VI, are used as standards in this method. Increasing amounts of the specific collagen are titrated into the patient's vWF sample. Changes in binding are observed and plotted against the collagen concentration. These results are then fitted to a single state binding model. The severity of the binding defect is reflected in the abnormality of the calculated binding constant. The assay also permits the determination of the specific vWF multimer that actually binds the collagen.

The invention in a further embodiment provides a vWF NORMANDY Assay using EQELS. At least 8 point mutations in vWF have been identified that result in defective binding of coagulation FVIII. The vWF Normandy assay enables rapid identification of patients having such FVIII binding deficiency mutations. The assay requires normal HMW vWF isolated from the patient, and purified coagulation FVIII. The purified coagulation FVIII is titrated into the vWF solution and the change in the coagulation FVIII mobility is observed. From this data a binding constant is calculated as in the preceding assay. The variance in the binding constant provides a measure of the severity of the coagulation FVIII binding defect.

The measurement of the vWF antigen relates to the amount of vWF present in the sample. Anti-vWF antibodies may be covalently linked to microbeads and the change in the microbead electrophoretic mobility may be observed as the vWF binds. The extent of the alteration in the bead electrophoretic mobility is generally proportional to the amount of vWF present in the sample.

In another embodiment, the present invention provides a Detection of Endothelium Activation or Damage Assay. Endothelium activation and endothelium damage are physiological events having high importance in a number of clinical situations, such as septicemia (viral, bacterial or fungal), acute coronary artery syndrome, veno-occlusive disease of the liver, drug mediated endothelium reactions, and acute inflammation. In this assay, vWF is purified from the patient and examined for high molecular weight vWF multimers as well as for the ultra large vWF multimers.

Figure 5:
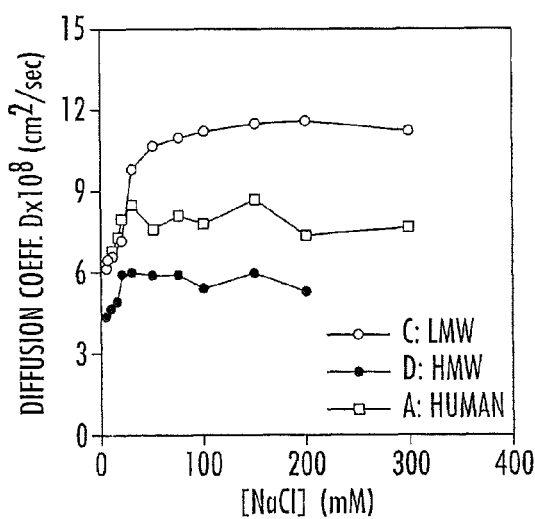
FIG. 5 is a plot illustrating the effect of ionic strength on the diffusion of vWF as determined by PCS.
Figure 6:
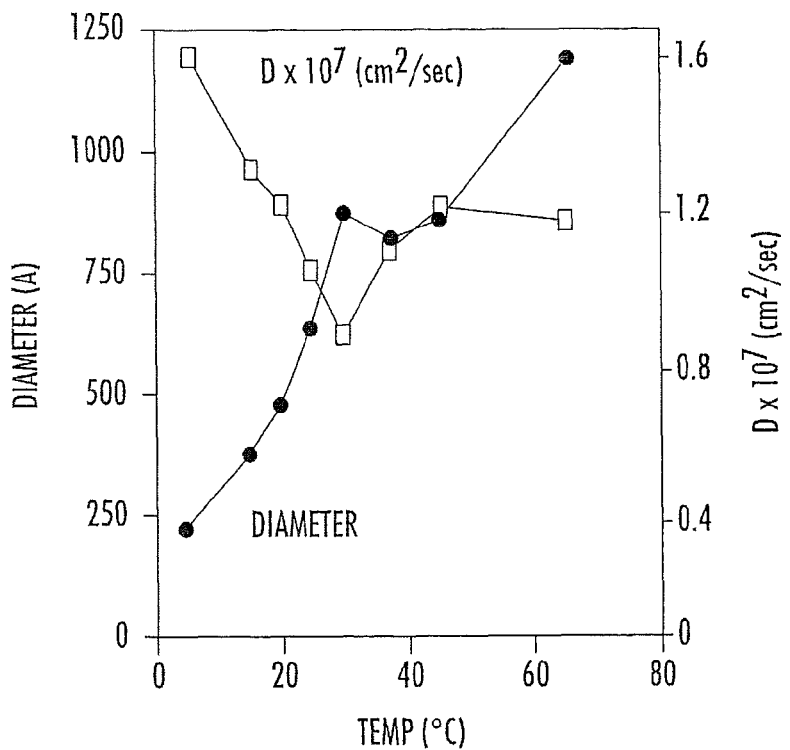
FIG. 6 is a plot illustrating the effect of temperature on the molecular shape of vWF based on spectroscopy techniques described herein.
Figure 7:
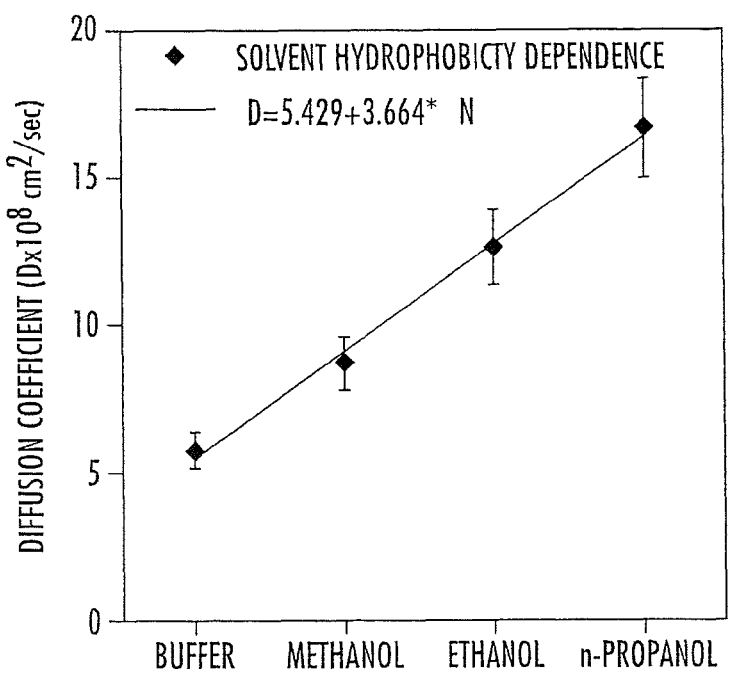
FIG. 7 is a plot illustrating the effect of solvent polarity on the molecular shape of vWF based on spectroscopy techniques described herein.

The data in FIGS. 5, 6 and 7 illustrate that when vWF is in a hydrophobic environment, extension occurs. As illustrated in FIG. 5, when the ionic strength is low, little counter ion screen is available to charged groups in vWF. Thus, the molecule is extended as evidenced by its lower diffusion coefficient. As the ionic strength is increased, better screen of the vWF surface charges is available so that vWF can assume a more compact shape as evidenced by its higher diffusion coefficient.

As shown in FIG. 6, changes in temperature influence hydrophobic bonding. When the temperature is low, vWF is more compact and has a smaller hydrodynamic diameter. As the temperature is increased, the diffusion coefficient decreases, which indicates that vWF is now more extended and is confirmed by the much larger hydrodynamic diameter.

With reference to FIG. 7, as the solvent becomes less polar, its dielectric constant increases. By the addition of linear alkane alcohols with increasing size, vWF becomes more compact as shown by the increase in its diffusion coefficient. Thus, the molecular shape of vWF can be altered by the solvent conditions.

The detection and characterization of vWF in the practice of the present invention advantageously employs vWF in an activated, extended state, as opposed to the compact, inactive state sometimes referred to as the "ball of yarn" state in which vWF is presumed to circulate in vivo. The extended, active state is preferred due to its much larger molecular dimension compared to the very compact conformation of the inactive state.

Accordingly, although the invention has been described herein with reference to various illustrative aspects, features and embodiments, it will be recognized that the invention is not thus limited, but rather extends to and encompasses other variations, modifications and alternative embodiments, such as will suggest themselves to those of ordinary skill in the art, based on the disclosure herein. The claims hereafter set forth therefore are intended to be broadly construed and interpreted as including all such variations, modifications and alternative embodiments within their spirit and scope.

That which is claimed is:

1. A method of diagnosing a patient for the presence or absence of a vWF abnormality and/or disease by analyzing the electrophoretic mobility distribution of von Willebrand factor (vWF) multimers in a biological sample obtained from the patient, comprising:
   a) obtaining a biological sample comprising a plurality of vWF multimers from a patient;
   b) electrophoretically separating said vWF multimers by electrophoretic mobility in said sample medium by placing said sample medium into a flow-through sample chamber and subjecting said sample medium in said flow-through sample chamber to an electric field to provide separated vWF multimers;
   c) exposing said separated vWF multimers in said sample medium in said flow-through sample chamber to a light source to produce scattered light;
   d) detecting said scattered light;
   e) determining the electrophoretic mobility distribution of said separated vWF multimers from said detected scattered light, and
   f) using the information from the electrophoretic mobility distribution to diagnose the presence or absence of a vWF abnormality or disease, wherein the presence or absence of a vWF abnormality or disease is identified by comparing said electrophoretic mobility distribution to parameters corresponding to a set of vWF abnormalities and/or diseases.

2. The method of claim 1, further comprising calculating the size and/or weight distribution of said separated vWF multimers from said detected scattered light.

3. The method of claim 1, wherein the vWF abnormality and/or disease is selected from the group consisting of Type I vWF disease, Type II vWF disease, Type III vWF disease, subtype IIA vWF disease, subtype IIB vWF disease, subtype IIM vWF disease, thrombotic thrombocytopenic purpura (TTP), and hemolytic uremic syndrome (HUS).

4. The method of claim 1, wherein said parameters are based on a plurality of spectra corresponding to said set of vWF abnormalities and/or diseases.

5. The method of claim 1, further comprising identifying an ADAMTS abnormality and/or disease based on said electrophoretic mobility distribution.

6. The method of claim 1, wherein said determining step is carried out by electrophoretic quasi elastic light scattering analysis.

7. The method of claim 1, wherein said determining step is carried out by:
   detecting a phase shift in the scattered light from a measured autocorrelation function;
   detecting a Doppler shift in scattered light compared to incident light; and then calculating the electrophoretic mobility of the scattering particle.

8. The method of claim 1, wherein said electrophoretically separating step, said exposing step, and said detecting step are carried out in a total time of less than 5 minutes.

9. The method of claim 1 wherein said determined electrophoretic mobility distribution includes vWF multimers having a molecular weight of 10 million or more.

10. The method of claim 1, wherein the step of obtaining a biological sample comprising a plurality of vWF multimers from a patient involves obtaining a plasma sample from the patient, and purifying vWF from the plasma sample to provide the sample medium.

* * * * *

UNITED STATES PATENT AND TRADEMARK OFFICE
CERTIFICATE OF CORRECTION

| | | |
|---|---|---|
| PATENT NO. | : 8,163,151 B2 | Page 1 of 1 |
| APPLICATION NO. | : 12/840445 | |
| DATED | : April 24, 2012 | |
| INVENTOR(S) | : Gabriel | |

It is certified that error appears in the above-identified patent and that said Letters Patent is hereby corrected as shown below:

Title Page:

Item (54) and Column 1, Line 2 and 3: Title, Please correct
"ASSAYS FOR DETECTION OF VON WILLEBRAND FACTOR (VWF) MULTIMERS AND FOR DEGRADATION OF VWF BY AGENTS SUCH AS ADAMTS13 AND RELATED METHODS"

to read: -- ASSAYS FOR DETECTION OF VON WILLEBRAND FACTOR (vWF) MULTIMERS AND FOR DEGRADATION OF vWF BY AGENTS SUCH AS ADAMTS13 AND RELATED METHODS --

Item (56) References Cited, Other Publications, Page 2, Right Column, Line 31, Tsai:
Please correct "Tsai, Km." to read -- Tsai, H.M. --

In the Patent:
Column 18, Lines 12 and 13: Please correct "IbN/IX" to read -- Ib/V/IX --

Signed and Sealed this
Sixteenth Day of October, 2012

David J. Kappos
*Director of the United States Patent and Trademark Office*